(12) United States Patent
Hahn et al.

(10) Patent No.: US 10,661,264 B2
(45) Date of Patent: *May 26, 2020

(54) MICROPARTICLES FOR CELL DISRUPTION AND/OR BIOMOLECULE RECOVERY

(71) Applicants: BOEHRINGER INGELHEIM RCV GMBH & CO KG, Vienna (AT); SANDOZ AG, Basel (CH)

(72) Inventors: Rainer Hahn, Vienna (AT); Alois Jungbauer, Vienna (AT); Alexandru Trefilov, Vienna (AT)

(73) Assignees: BOEHRINGER INGELHEIM RCV GMBH & CO KG, Vienna (AT); SANDOZ AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/103,473

(22) Filed: Aug. 14, 2018

(65) Prior Publication Data

US 2019/0046969 A1    Feb. 14, 2019

Related U.S. Application Data

(63) Continuation of application No. 14/913,337, filed as application No. PCT/EP2014/068015 on Aug. 25, 2014, now Pat. No. 10,076,749.

(30) Foreign Application Priority Data

Aug. 23, 2013 (EP) ..................................... 13181537
Aug. 23, 2013 (EP) ..................................... 13181540

(51) Int. Cl.

| | |
|---|---|
| *B01J 39/20* | (2006.01) |
| *B01J 39/04* | (2017.01) |
| *C12N 9/02* | (2006.01) |
| *C07K 1/18* | (2006.01) |
| *B01J 39/26* | (2006.01) |
| *B01J 41/14* | (2006.01) |
| *B01J 41/20* | (2006.01) |
| *B01J 47/04* | (2006.01) |
| *B01J 39/05* | (2017.01) |
| *B01J 39/07* | (2017.01) |
| *B01J 41/05* | (2017.01) |
| *B01J 41/07* | (2017.01) |
| *B01D 15/36* | (2006.01) |
| *C07K 14/435* | (2006.01) |
| *C07K 16/00* | (2006.01) |

(52) U.S. Cl.
CPC ............ *B01J 39/20* (2013.01); *B01D 15/362* (2013.01); *B01D 15/363* (2013.01); *B01J 39/04* (2013.01); *B01J 39/05* (2017.01); *B01J 39/07* (2017.01); *B01J 39/26* (2013.01); *B01J 41/05* (2017.01); *B01J 41/07* (2017.01); *B01J 41/14* (2013.01); *B01J 41/20* (2013.01); *B01J 47/04* (2013.01); *C07K 1/18* (2013.01); *C07K 14/43595* (2013.01); *C07K 16/00* (2013.01); *C12N 9/0089* (2013.01); *C12Y 115/01001* (2013.01)

(58) Field of Classification Search
None
See application file for complete search history.

(56) References Cited

U.S. PATENT DOCUMENTS

| | | | |
|---|---|---|---|
| 7,947,813 B2 | 5/2011 | Fahrner et al. | |
| 10,076,749 B2 * | 9/2018 | Hahn ...................... | C07K 1/18 |
| 2004/0118681 A1 | 6/2004 | Hellinga et al. | |
| 2007/0184534 A1 | 8/2007 | Berry et al. | |
| 2011/0003367 A1 | 1/2011 | Tajima et al. | |
| 2012/0165511 A1 | 6/2012 | Arunakumari et al. | |
| 2016/0193598 A1 | 7/2016 | Hahn et al. | |

FOREIGN PATENT DOCUMENTS

| | | |
|---|---|---|
| JP | 2009-247244 | 10/2009 |
| WO | WO 86/06727 A1 | 11/1986 |

OTHER PUBLICATIONS

JP, 2016-535505 Office Action, dated Jul. 10, 2018.
WO, PCT/EP2014/068015 ISR and Written Opinion, dated Jan. 21, 2015.
Aspelund, M. T., "Membrane-based separations for solid/liquid clarification and protein purification", Doctoral Dissertation, Iowa State University, 2010, pp. 1-149.
Krizkova, S., et al., "Rapid superparamagnetic-beads-based automated immunoseparation of Zn-proteins from *Staphylococcus aureus* with nanogram yield", Electrophoresis, 2013, vol. 34, pp. 224-234.
Paril, C., et al., "Adsorption of pDNA on microparticulate charged surface", Journal of Biotechnology, 2009, vol. 141, pp. 47-57.
Rounds, M. A., et al., "Poly(Strene-Divinylbenzene)-Based Strong Anion-Exchanfe Packing Material for High-Performance Liquid Chromatography of Proteins", Journal of Chromatography, 1987, vol. 397, pp. 25-38.

* cited by examiner

*Primary Examiner* — Anand U Desai
(74) *Attorney, Agent, or Firm* — One LLP

(57) ABSTRACT

The present invention provides novel methods of cell disruption and release of biomolecules from a cell. The invention comprises the use of positively and/or negatively charged microparticles comprising ground resin. It is particularly useful for purification of biomolecules from cell culture.

14 Claims, 17 Drawing Sheets

Marathon MSC  Marathon A2  Amberlite IRC748  Amberlite IRA458

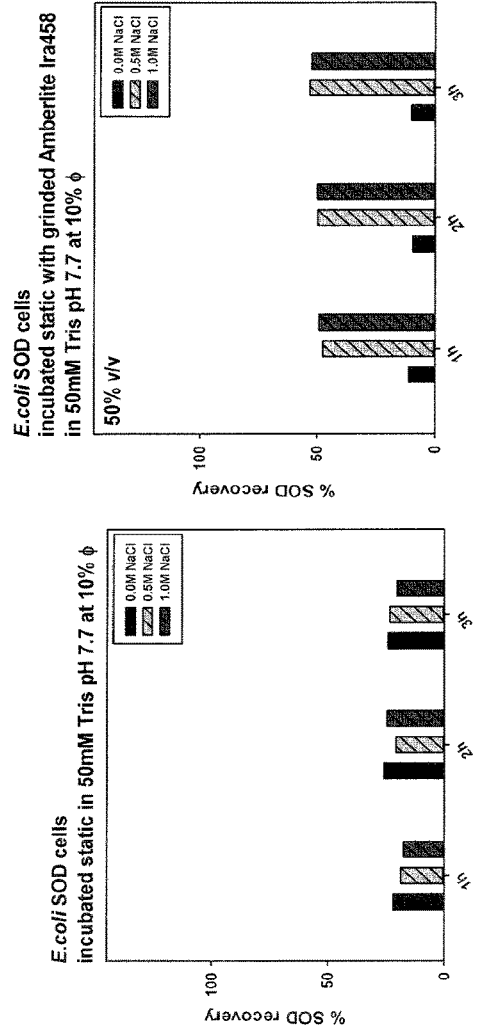
Fig. 11A
Fig. 11B
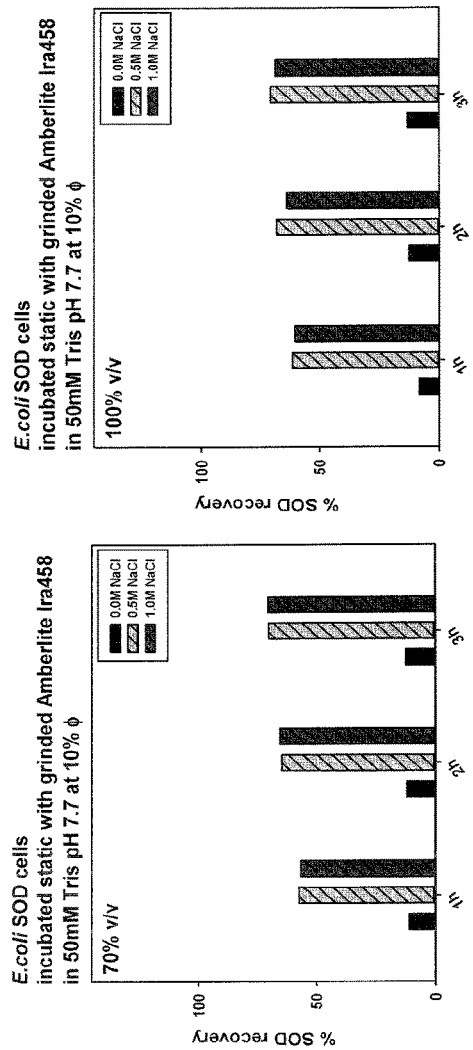
Fig. 11C
Fig. 11D

Fig. 16A                    Fig. 16B

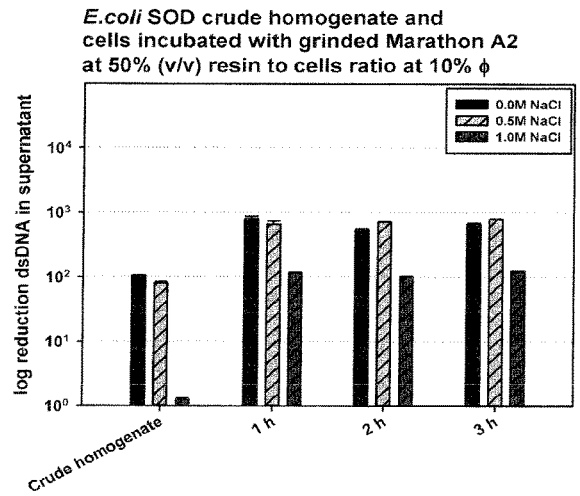
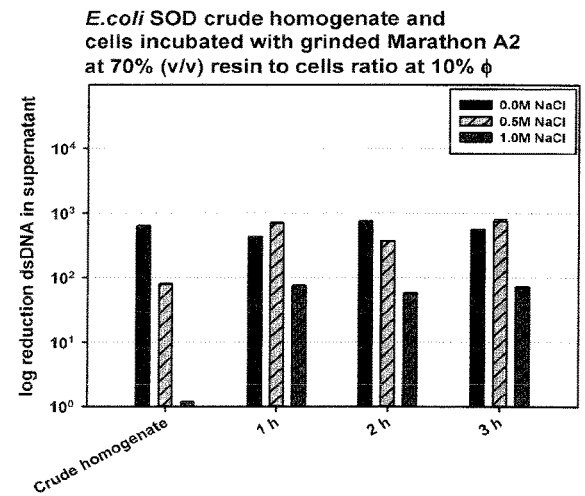
Fig. 16D
Fig. 16E
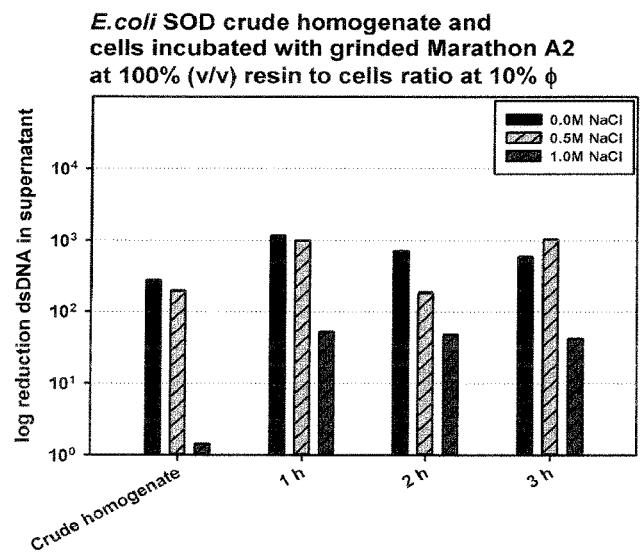
Fig. 16F

MICROPARTICLES FOR CELL DISRUPTION AND/OR BIOMOLECULE RECOVERY

CROSS-REFERENCE TO RELATED APPLICATIONS

The present application is a continuation of U.S. Non-Provisional application Ser. No. 14/913,337, filed Feb. 19, 2016, which is a National Phase Patent Application of International Patent Application Number PCT/EP2014/068015, filed on Aug. 25, 2014, which claims priority to European Patent Application No. 13181540.9, filed on Aug. 23, 2013 and European Patent Application No. 13181537.5, filed on Aug. 23, 2013, all of which are hereby incorporated by reference.

FIELD OF INVENTION

The present invention generally relates to the field of biomolecule recovery and cell disruption, and particularly to the recovery of intracellular biomolecules such as polypeptides or polynucleotides from cell suspensions. It covers methods of recovering biomolecules from fluids such as biological fluids. In a further aspect, the present invention is related to the field of cell culture and purification of biomolecules from cell culture.

BACKGROUND OF THE INVENTION

Despite all previous efforts to develop artificial production systems, biological entities such as cells are unrivalled in their ability to produce complex substances such as antibiotics, proteins and nucleic acids. Nearly all substances of cellular origin produced industrially today are extracellular products that are produced within the cell and subsequently excreted into the environment. However, a large proportion of potentially useful substances remain intracellular. In order to release the intracellular material, cells are typically disintegrated by mechanical, physical, chemical or enzymatic means. The recovery efficiency of valuable cellular products is closely linked to their formation, location and their interactions within the biological system. In the past decades, investigations of molecular structures and their functionality within these cellular systems have enhanced the diversification of such products and their large-scale processing. At the same time, requirements regarding product quality, especially in the healthcare sector, resulted in the necessity to deliver well defined, effective and highly pure substances.

Current methods for cell disruption include mechanical and non-mechanical methods. Non-mechanical methods comprise physical (decompression, osmotic shock, thermolysis, freeze drying, microwave), chemical (antibiotics, chelating agents, detergents, solvents, alkalis, supercritical $CO_2$) and enzymatic (lysis, autolysis, phages) methods. On the other hand, mechanical approaches and devices for cell disruption comprise bead milling, homogenisers, cavitation (ultrasonic, hydrodynamic) and microfluidizers. Only some cell disruption methods (mainly mechanical) are performed at an industrial scale, where they are commonly integrated in downstream (e.g. recovery, purification) processing.

For large scale, the most common mechanical methods are bead milling and high pressure homogenisation which are typically implemented as standard operations. When using high pressure homogenisation, a cell solution is forced through a narrow valve under high pressure. By passing through the valve, cells are subjected to turbulence, cavitation, high shear forces and a sudden pressure drop upon discharge which tear the cells apart. The stress and erosion of the valve must be considered in the construction and increase with the rising homogenising pressure. Further, the temperature of the solution rises with increasing pressure, rendering the method energy-consuming and making cooling of the device and the suspension necessary, particularly when temperature-labile enzymes are released. Approximately more than 90% of the power consumed by the homogeniser dissipates as heat, and the cooling cost represents a large portion of the total costs for cell disintegration. Further, successive passages are often required in order to achieve sufficiently high yields (Kula et al., "Purification of Proteins and the Disruption of Microbial Cells." Biotechnology Progress 1987).

In bead milling, beads are added to a biological fluid which is subsequently subjected to high speed agitation by stirring or shaking. By collision with beads cells are disrupted and intracellular contents are released. Bead milling also produces heat and requires cooling. It is a rather complex process influenced by a variety of parameters, including construction of the bead mill, operational parameters and product specific properties. Construction and geometry of the bead mill are crucial process variables. However, smaller versions are often geometrically dissimilar to industrial-scale bead mills, which complicates the extrapolation of data from laboratory trials to batch performance (Kula et al., "Purification of Proteins and the Disruption of Microbial Cells." Biotechnology Progress 1987).

Mechanical disruption methods suffer from several drawbacks. Because cells are entirely disrupted, all intracellular materials are released, thereby increasing the contaminants content of the intermediate product. Thus, the product of interest must be separated from a complex mixture of proteins, nucleic acids, and cell fragments. In addition, released nucleic acids may increase the viscosity of the solution and may complicate subsequent processing steps such as chromatography. The cell debris produced by mechanical disintegration often consists of small cell fragments, making the solution difficult to clarify. Complete product release often requires more than one pass through the disruption device, which exacerbates the problem by further reducing the size of the fragments. These are difficult to be removed by continuous centrifugation, because the throughput of the device is inversely related to the square of the particle diameter. Filtration is complicated by the sticky nature of the homogenate and by its tendency to foul membranes. Furthermore, mechanical methods require regular maintenance and costly equipment and are energy consuming. They generate heat and require extensive cooling in order to be usable for temperature-sensitive enzymes. Further, they expose the cells and therefore the extracted products to high shear stress. Most products will be denatured by the heat generated unless the device is sufficiently cooled.

As mentioned above, more selective release methods involve physical, chemical or enzymatic treatment. Chemical treatment involves the use of EDTA, chaotropic agents, organic solvents, antibiotics, acids, alkalis and surfactants. Besides the problem of waste disposal of excess chemicals, these methods are rather expensive and thus not suitable for large-scale application. Contamination of the desired product with the chemicals is another drawback. Some chemicals are not very selective and tend to damage sensitive proteins, enzymes and the cells walls.

Enzymatic cell disruption is more specific but is often limited when applied to complex cell structures with several distinct layers such as bacterial cell walls. Further, it is restricted by the cost of enzyme and buffers. Thus, enzymatic treatment is not applicable at large or industrial scale either. Another drawback is the potential contamination of the desired product with the enzyme.

Physical permeabilization can be accomplished by freeze-thawing or osmotic shock treatment. With freeze-thawing, multiple cycles are necessary for efficient product release, and the process can be quite lengthy. Osmotic shock treatment, on the other hand, may not be sufficient to disrupt cells with robust cell wall structures.

In sum, disadvantages of these methods include comparably high costs, low practicability at large scale, low efficiency and reproducibility, and the necessity to remove added substances after the release.

Taking into account the potential of cellular production systems, there is a need for alternative methods for recovering biomolecules, in particular from cell suspensions, which are easy to handle, cost-efficient, and scalable. Further, the methods should be gentle enough for sensitive biomolecule products and enable a highly selective biomolecule recovery which yields a product with low contamination. It is therefore one objective of the present invention to provide a method or system which overcomes one or more of the above mentioned drawbacks.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising" will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein, "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

SUMMARY

The present invention provides novel methods for obtaining biomolecules, also referred to as biomolecule recovery which overcomes one or more of the above mentioned drawbacks. The method can be used to obtain biomolecules from liquids and fluids, such as cell cultures, cell homogenates, cell lysates, cell suspensions, fermentation broth, culture broth, fermentation supernatant, culture supernatant, cell supernatants, such as from *E. coli, Pichia pastoris*, and CHO cell culture. Further, the present invention involves methods of cell disruption which can be used to release biomolecules contained in cells. As will be shown in the description, the present invention is particularly useful for the disruption of cells and recovery of intracellular biomolecules. The methods disclosed herein are simple, cost-efficient, and readily scalable for industrial application. The methods provide a simple process for selective recovery of biomolecules, where neither complex equipment nor soluble additives, excepting buffer and salt, are required. As described earlier, prior art methods for biomolecule recovery from cell suspensions involve either mechanical stress and/or chemical additives. In contrast to conventional methods applied at industrial scale today, the methods of the present invention are gentle and do not subject the cells and/or the desired biomolecule products to harsh conditions. Thus, the methods disclosed herein reduce the amount of contaminating debris and exert less potentially harming mechanical and physical stress on the desired biomolecules.

The inventors have surprisingly discovered that charged microparticles or hydrophobic microparticles comprising ground resin can act to recover (herein also referred to as "to extract") biomolecules from biological fluids. Further, in some embodiments, when added to a cell suspension, charged microparticles can disrupt cells and at the same time adsorb the biomolecules released from the cells. Therefore, in one aspect the microparticles can be used to disrupt cells and release biomolecules and further adsorb the biomolecules in a simple and scalable manner. In some aspects, the microparticles have been found to form flocs upon interaction with cells and/or biomolecules and/or counter charged microparticles and can be easily separated from the biological fluid. The released biomolecules can thus easily be recovered by separating the flocs with biomolecules adsorbed thereon. The present invention thus further provides simplified methods where the steps of cell disruption and biomolecule extraction in the downstream processing are combined. This technique is termed colloidal solid phase extraction (CSPE). Without being bound by theory, it is assumed that positively charged microparticles derived from an anion-exchange resin build flocs with cells by adsorbing to the negatively charged cell surface, thereby displacing cations, in particular calcium and/or magnesium ions, which are associated with the usually negatively charged cell surface of particularly bacterial cells. As a result, the lining up of the molecules building the cell membrane becomes somehow destabilized and thus cell become leaky.

In case of a negatively charged particles derived from a chelating cation exchange resin, it is assumed that such particles bind cations, in particular calcium and/or magnesium, thereby destabilizing the lining up of the molecules building the cell membrane. For hydrophobic microparticles, it was also found that they form flocs.

This is currently a unique method for extraction of intracellular biomolecules by gently "opening" the cell with low fragmentation of the cellular structures (e.g. cell walls), resulting in a reduction in contaminants levels. At the same time, this novel technique allows for selective biomolecule extraction, and is comparable to mechanical disruption methods known in the art, e.g. high pressure homogenisation and bead milling, in terms of efficiency, but offers a higher selectivity and a lower contamination level. At the same time, using the novel method disclosed herein, it is possible to maintain the integrity of the cells while the desired biomolecule is recovered. Thus, "opening" cells means that cells, however are preferably not entirely disrupted. Accordingly, the "opening" preferably means that cells become leaky and thus their cytoplasmic contents leak out.

In a first aspect, the invention provides the novel use of positively charged microparticles and/or negatively charged microparticles for biomolecule recovery, wherein the positively charged microparticles comprise ground polymeric anion-exchange resin, and wherein the negatively charged microparticles comprise ground polymeric cation exchange resin. In one embodiment, only positively charged microparticles are used. In another embodiment, only negatively charged microparticles are used. In a further embodiment, both positively charged microparticles and negatively charged microparticles are used.

In a second aspect of the invention, the composition comprises hydrophobic microparticles. These hydrophobic microparticles are capable of adsorbing in particular peptides or polypeptides, but also other biomolecules. The mechanism for adsorption is thought to be based primarily on hydrophobic (Van der Weals, London Type) attractions between the hydrophobic portions of the adsorbed ligands such as peptides or polypeptides and the polymeric surface of the microparticles.

The microparticles are obtainable (can be obtained) by grinding resin as described herein, for example, by grinding ion-exchange resin and optionally conditioning the ground resin. Such particles are referred to herein as "microparticles," "adsorbent particles", "adsorbent", "particles", "ground particles", or "ground resin". These terms are used interchangeably. Preferably, the microparticles are obtained by grinding conventional large-diameter small-pore particles which are usually intended for water de-ionization and waste water treatment.

The positively charged microparticles can be prepared by grinding anion exchange resin. The anion-exchange resin can be weakly or strongly basic. Likewise, cation-exchange resin can be used to prepare the negatively charged microparticles. The cation exchange resin can be weakly or strongly acidic. In some embodiments of the present invention, the cation-exchange resin and/or the anion-exchange resin can be a chelating resin The ion-exchange resin according to the present invention can be based on any suitable material. Preferably, the resin is polystyrene-based, Hydroxyethyl methacrylate (HEMA)-based, dimethylamino ethylmethacrylate (DMAEMA)-based, dimethylamino ethylmethacrylate (pDMAEMA) based, polyacrylamide based or methacrylic acid (MAA) based. More preferably, the resin is polystyrene cross-linked with divinylbenzene (DVB).

Preferably, the microparticles are in the form of ground particles having an average particle size less than about 10 µm, such as less than about 5 µm.

Microparticles according to the present invention can be obtained by grinding anion-exchange resin or cation exchange resin. Anion-exchange resin may be, for example, AMBERLITE® IRA-400, AMBERLITE® IRA-485, DOWEX® 1×2-100, DOWEX® 1-8-100, DIAION® SA 20A, MARATHON® A2 or other anion-exchange resin known in the art. Cation exchange resin may be, for example, AMBERLITE® IRC-748, DOWEX® 50 WX2-100, DOWEX® 50 WX8-100, DIAION® SK 110, MARATHON® MSC, or other cation-exchange resin known in the art. Preferred anionic exchange resins include AMBERLITE® IRA-458 and MARATHON® A2. Preferred cationic exchange resins include AMBERLITE® IRC-748.

In another aspect, the present invention provides the use of positively charged microparticles and/or negatively charged microparticles or hydrophobic microparticles disclosed herein to adsorb biomolecules, preferably proteins or polynucleotides, such as DNA, e.g., plasmid DNA, cosmid DNA, BAC DNA, YAC DNA, mini-circle DNA from a fluid. The fluid is a biological fluid such as cell homogenate, fermentation supernatant, fermentation broth, culture broth, culture supernatant, cell lysate or a cell suspension.

Further, the present invention provides the use of the microparticles disclosed herein for cell disruption. Preferably, the disrupted cells release biomolecules which adsorb to the microparticles. The cells for disruption include eukaryotic and prokaryotic cells. In one embodiment, the cell is a prokaryotic cell. The cell can be selected from the group including, but not limited to, Enterobacteriaceae, Pseudomonaceae, Lactobacteriacea, or Bacillaceae. In one preferred embodiment, the cell is *E. coli*.

In a further aspect, the present invention provides a method for obtaining biomolecule, comprising adding the positively charged microparticles and/or negatively charged microparticles or hydrophobic microparticles described herein to a biological fluid and recovering the biomolecules from the biological fluid. In some embodiments, the method further comprises allowing the microparticles to form flocs, removing the flocs from the biological fluid, and desorbing the biomolecules from the flocs. In some instances, depending on the biomolecule to be recovered, the microparticles can be used to form flocs with unwanted cellular structure and the biomolecule is recovered in the fluid after the flocs are removed. The flocs can be removed from the biological fluid by, for example, centrifugation or filtration. In one embodiment, the biological fluid is agitated during and/or after adding the microparticles and/or during desorbing the biomolecules from the flocs or the biological fluid.

The present invention further provides a method of disrupting cells, comprising adding charged and/or hydrophobic microparticles to a cell suspension. Said charged microparticles can be positively charged and/or negatively charged. In some aspects, the method further comprises releasing biomolecules from the cells. In addition, the present invention also provides a biological fluid and positively charged microparticles and/or negatively charged microparticles or hydrophobic microparticles.

The exact nature of this invention, as well as its advantages, will become apparent to a skilled person from the following description and examples. The present invention is not limited to the disclosed preferred embodiments or examples. A skilled person can readily adapt the teaching of the present invention to create other embodiments and applications.

BRIEF DESCRIPTION OF THE DRAWINGS

FIG. 11A shows the SOD recovery in the absence of acrylic IRA 458. FIG. 11B shows the SOD recovery using 50% v/v resin:cells ratio of acrylic IRA 458. FIG. 11C shows the SOD recovery using 75% v/v resin:cells ratio of acrylic IRA 458. FIG. 11D shows the SOD recovery using 100% v/v resin:cells ratio of acrylic IRA 458. SOD amount was determined by SDS-Page densitometry after 1-3 hours static incubation in 50 mM TRIS (pH 8.0) at various concentrations of NaCl (1.0 M, 0.5 M, and 0 M).

FIG. 16A shows the dsDNA reduction kinetics during extraction of protein (SOD) using 50% v/v resin:cells of AMBERLITE® IRA458. FIG. 16B shows the dsDNA reduction kinetics during extraction of protein (SOD) using 70% v/v resin:cells of AMBERLITE® IRA458. FIG. 16D shows the dsDNA reduction kinetics during extraction of protein (SOD) using 50% v/v resin:cells of MARATHON® A2. FIG. 16E shows the dsDNA reduction kinetics during extraction of protein (SOD) using 70% v/v resin:cells of MARATHON® A2. FIG. 16F shows the dsDNA reduction kinetics during extraction of protein (SOD) using 100% v/v resin:cells of MARATHON® A2. All experiments used E. coli homogenate and cell suspension (10% v/v) after static incubation (50 mM TRIS, pH 8.0) with the various microparticle resins and subsequent elution with NaCl. DNA amount was estimated with "Pico Green QuantIt" assay from Invitrogen.

ITEMS OF THE INVENTION

Figure 1:
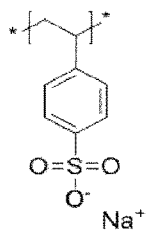
FIG. 1: Schematic chemical structure of functional groups and their binding sites to polymer matrix for MARATHON® MSC (MMSC), MARATHON® A2 (MA2), AMBERLITE® IRC748 and AMBERLITE® IRA458.
Figure 1:
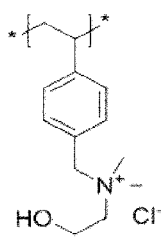
Figure 1:
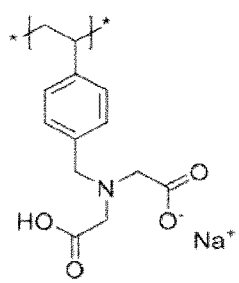
Figure 1:
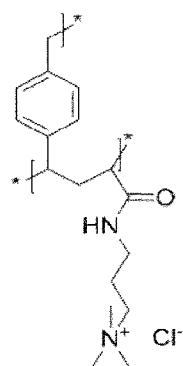

The present invention can also be characterized by the following items:

1. Use of positively charged microparticles and/or negatively charged microparticles for biomolecule recovery, wherein the positively charged microparticles comprise ground polymeric anion-exchange resin, and wherein the negatively charged microparticles comprise ground polymeric cation exchange resin, wherein the biomolecule is preferably a polypeptide or a polynucleotide.

2. Use of a positively charged microparticles and/or negatively charged microparticles for cell disruption, wherein the positively charged microparticles comprise ground polymeric anion-exchange resin, and wherein the negatively charged microparticles comprise ground polymeric cation exchange resin.

3. Use of hydrophobic microparticles for biomolecule recovery.

4. The use of item 1 or 2, wherein the cation exchange resin is weakly or strongly acidic.

5. The use of item 1 or 2, wherein the anion-exchange resin is weakly or strongly basic.

6. The use of item 1 or 2, wherein the cation exchange resin and/or the anion-exchange resin is a chelating resin.

7. The use of any one of the preceding items, wherein the anion-exchange resin and the cation exchange resin is polystyrene-based, Hydroxyethyl methacrylate (HEMA)-based, dimethylamino ethyl methacrylate (DMAEMA)-based, dimethylamino ethyl methacrylate (pDMAEMA), polyacrylamide based, methacrylic acid (MAA)-based.

8. The use of any one of the preceding items, wherein the cation exchange resin and anion-exchange resin is polystyrene cross-linked with divinylbenzene.

9. The use of any one of the preceding items, wherein the microparticles have an average particle size of less than about 5 μm.

10. The use of any one of the preceding items, wherein the positively charged microparticles or negatively charged microparticles are obtainable by grinding a polymeric anion-exchange and/or cation-exchange resin.

11. The use of any one of the preceding items, wherein the anion-exchange resin is AMBERLITE® IRA-400, AMBERLITE® IRA-485, DOWEX® 1×2-100, DOWEX® 1-8-100, MARATHON® A2 or DIAION® SA 20A.

12. The use of any one of the preceding items, wherein the cation exchange resin is AMBERLITE® IRC-748, DOWEX® 50 WX2-100, DOWEX® 50 WX8-100, MARATHON® MSC or DIAION® SK 110.

13. The use of any one of the preceding items, wherein the resin is non-porous.

14. The use of any one of the preceding items, wherein the cell is a eukaryotic or prokaryotic cell.

15. The use of any one of items 1 to 14, wherein the cell is selected from Enterobacteriaceae, Pseudomonaceae, Lactobacteriacea, or Bacillaceae.

16. The use of item 14 or 15, wherein the cell is *E. coli*.

17. The use of any one of the preceding items, wherein the biomolecule is a protein or a polynucleotide.

18. A method of obtaining biomolecules from a biological fluid comprising a) adding a positively charged microparticles and/or negatively charged microparticles or hydrophobic microparticles as defined in any one of items 1 to 13 to a biological fluid, and recovering the biomolecules from the biological fluid.

19. The method of item 18, further comprising: b) allowing the microparticles to form flocs c) removing the flocs from the biological fluid and d) desorbing the biomolecules.

20. The method of item 19, wherein the biological fluid is a cell suspension, fermentation broth, culture broth, a cell homogenate or fermentation supernatant.

21. The method according to any of items 18 to 20, wherein the method further comprises agitating the biological fluid after step a) and/or d).

22. The method according to any of items 18-21 wherein step c) is carried out by a separation technique, such as centrifugation or filtration.

23. The method according to any of items 18-22, wherein the cation exchange resin is weakly or strongly acidic.

24. The method according to any of items 18-22, wherein the anion-exchange resin is weakly or strongly basic.

25. The method according to any of items 18-22, wherein the cation exchange resin and/or the anion-exchange resin is a chelating resin.

26. The method according to any of items 18-25, wherein the anion-exchange resin and the cation exchange resin is polystyrene-based, Hydroxyethyl methacrylate (HEMA)-based, dimethylamino ethyl methacrylate (DMAEMA)-based, dimethylamino ethyl methacrylate (pDMAEMA), polyacrylamide based, methacrylic acid (MAA)-based.

27. The method according to any of items 18-26, wherein the cation exchange resin and anion-exchange resin is polystyrene cross-linked with divinylbenzene.

28. The method according to any of items 18-28, wherein the microparticles have an average particle size of less than about 5 μm.

29. The method according to any of items 18-28, wherein the positively charged microparticles or negatively charged microparticles are obtainable by grinding a polymeric anion-exchange and/or cation-exchange resin.

30. The method according to any of items 18-29, wherein the anion-exchange resin is AMBERLITE® IRA-400, AMBERLITE® IRA-485, DOWEX® 1×2-100, DOWEX® 1-8-100, MARATHON® A2 or DIAION® SA 20A.

31. The method according to any of items 18-30, wherein the cation exchange resin is AMBERLITE® IRC-748, DOWEX® 50 WX2-100, DOWEX® 50 WX8-100, MARATHON® MSC or DIAION® SK 110.

32. The method according to any of items 18-31, wherein the resin is non-porous.

33. The method according to any of items 18-32, wherein the cell is a eukaryotic or prokaryotic cell.

34. The method according to any of items 18-33, wherein the cell is selected from Enterobacteriaceae, Pseudomonaceae, Lactobacteriacea, or Bacillaceae.

35. The method according to item 34, wherein the cell is *E. coli*.

36. The method according to any of items 18-35, wherein the biomolecule is a protein or a polynucleotide.

37. A method of disrupting cells comprising adding positively charged and/or negatively charged microparticles or hydrophobic microparticles to a cell suspension.

38. The method of item 37, further comprising releasing of biomolecules from the cells.

39. The method of item 37 or 38, wherein the biomolecule is a polypeptide or polynucleotide.

40. A biological fluid comprising positively charged microparticles and/or negatively charged microparticles or hydrophobic microparticles, wherein the positively charged microparticles comprise ground polymeric anion-exchange resin, and wherein the negatively charged microparticles comprise ground polymeric cation exchange resin.

41. The fluid of item 40 further comprising flocs.

42. Use of positively charged microparticles for biomolecule recovery, wherein the positively charged microparticles comprise ground polymeric anion-exchange resin, and wherein the biomolecule is acidic or basic.

43. Use of item 42 for biomolecule recovery from cell lysate or cell homogenate.

44. Use of item 42 for biomolecule recovery from cell suspension.

45. Use of negatively charged microparticles for biomolecule recovery, wherein the negatively charged microparticles comprise ground polymeric cation exchange resin, and wherein the biomolecule is acidic or basic.

46. Use of item 45 for biomolecule recovery from cell lysate or cell homogenate.

47. Use of item 45 for biomolecule recovery from cell suspension.

48. Use of positively and negatively charged microparticles for biomolecule recovery, wherein the positively charged microparticles comprise ground polymeric anion-exchange resin and negatively charged microparticles comprise ground polymeric cation exchange resin, and wherein the biomolecule is acidic or basic.

49. Use of item 48 for biomolecule recovery from cell lysate or cell homogenate.

50. Use of item 48 for biomolecule recovery from cell suspension.

51. Use of positively charged microparticles for cell disruption and release of biomolecule from the cell, wherein the positively charged microparticles comprise ground polymeric anion-exchange resin, and wherein the biomolecule is acidic or basic.

52. Use of negatively charged microparticles for cell disruption, wherein the negatively charged microparticles comprise ground polymeric cation exchange resin, and wherein the biomolecule is acidic or basic.

53. A method of obtaining biomolecules from a biological fluid comprising a) adding positively charged microparticles and/or negatively charged microparticles to a biological fluid, and recovering the biomolecules from the biological fluid, wherein the biomolecule is acidic or basic.

54. The method of item 53 wherein the biological fluid is a cell suspension, cell lysate or cell homogenate.

55. A method of obtaining biomolecules from a cell, comprising a) adding positively charged microparticles and/or negatively charged microparticles to disrupt the cell, thereby releasing the biomolecule from the cell, and b) recovering the released biomolecules.

56. The method of item 55, wherein the biomolecule is acid or basic.

57. The method of item 55, wherein positively charged microparticles is added.

58. The method of item 55, wherein negatively charged microparticles is added.

DETAILED DESCRIPTION OF THE INVENTION

The present invention provides methods for biomolecule recovery and/or for cell disruption that are simple and fast using the charged or hydrophobic microparticles as described herein. It is partly based on the surprising finding that the microparticles, in particular the charged microparticles can disrupt cells and can further release and adsorb biomolecules from the cells, thus enabling a fast and efficient recovery of biomolecules. Moreover, it has been found that charged microparticles rapidly form flocs of large diameters (such as at least 5 μm) when added to a biological fluid such that the microparticles can interact with/adsorb to cells and/or adsorb biomolecules, which allows an easy separation of the biomolecules adsorbed to the microparticles and/or flocks built by the microparticles and the biomolecules. The same is true for hydrophobic microparticles.

As will be appreciated by a skilled person in the art, the present invention is particularly useful for separating proteins or plasmids from biological fluids such as cell suspensions in large scale applications including pilot or industrial scale as described herein. The charged and/or hydrophobic microparticles can advantageously be used in batch process (referred herein as "batch adsorption").

Moreover, the novel methods described herein provides high recovery efficiency and low contaminants levels. The present invention can advantageously be applied for recovering biomolecules especially if the biomolecules are temperature or shear sensitive and prone to denaturation when conventional methods of biomolecule extraction are applied.

Cells and Biomolecules

As described earlier, the present invention provides methods for biomolecule recovery from a fluid such as a biological fluid. In some embodiments, the methods of the present invention involve the disruption of cells in the biological fluid and the release of biomolecules from the cells. The biomolecules are preferably intracellular biomolecules such as proteins or plasmids. The released biomolecules can be subsequently recovered from the biological fluid.

As defined herein, the term "intracellular" refers any substance found within a cell. A "biomolecule" as defined herein includes any molecule that are normally found in or synthesized by a cell, including polypeptides or polynucleotides. The biomolecules may be acidic or basic biomolecules. Examples of biomolecules include but are not limited to oligosaccharide, polysaccharide, lipopolysaccharide, oligopeptides, proteins, nucleosides, flavonoids, oligonucleotides, DNA (ds or ssDNA), plasmid DNA, RNA (ds or ssRNA), organometallic compounds, amino acids, lipids, pyrimidines, purines, carbohydrates, peptidomimetic compounds, toxins, steroids and enzymes.

A "cell" when used herein refers to a cell, preferably a "host cell," which is capable of producing (expressing) a biomolecule. Such cells can be applied in the methods of the present invention. A foreign nucleotide sequence can be introduced in the cell for producing the biomolecule.

Cells or host cells that can be used in the method of the present invention can be either prokaryotic cells, eukaryotic cells, or both. More preferably, the cell used in the methods of the present invention are vertebrate cells including mammalian, avian, amphibian and fish cells and insect cells. Also included by cells or host cells are eukaryotic cells. Typically, eukaryotic cells are mammalian cells, avian cells or insect cells. A cell or host cell also includes yeast cell or fungal cells. However, it is preferred that the host cell is a prokaryotic cell including bacterial cells from Gram-negative bacteria such as cells from Enterobacteriaceae, e.g. *E. coli*, or Pseudomonadaceae, e.g. *P. putida*, or Gram-positive bacteria such as cells from Lactobacteriaceae or Bacillaceae. Most preferably however, the host cell is *E. coli*.

Microparticles

"Charged" microparticles as defined herein are positively charged microparticles and/or negatively charged microparticles. "Positively charged" microparticles have at least one elementary charge of a proton, and more typically more than one, at a neutral pH. "Negatively charged" microparticles have at least one elementary charge of an electron, and more typically more than one, at a neutral pH.

The microparticles can comprise ground resin. Resin useful for the present invention is a solid, non-soluble polymeric material which is capable of interacting and attaching to various elements and allows for capturing of the elements from a mixture. Resins are generally composed of inert compound including, but not limited to, sephadex, polystyrene, polyacrylamide, polymethacrylate or neutral polysaccharides. They may also include cross-linked natural polymers like cellulose, dextran or agarose.

Microparticles according to preferred embodiments are prepared from ion-exchange resin, more preferably, polymeric anion-exchange resin and/or cation-exchange resin. Ion exchange resin refers to a solid support containing insoluble carrier of an electrical charge polymers carrying fixed functional groups or sites with exchangeable ions. Illustrative examples of suitable ion exchange resins for preparing microparticles include anion exchange resins, cation exchange resins, and mixed-mode chromatography resins, also sometimes referred to herein as mixed-mode ion exchange resins. The exchangeable ion form is generally one or more of $Na^+$, $H^+$, $OH^-$, or $Cl^-$ ions, depending on the type of ion exchangeable resin. Ion exchange resin includes weak and strong acid cation exchange resins as well as weak and strong base anion exchange resins. Suitable ion exchange resins further include chelating resins.

Ion exchange resins are widely used in various industrial fields. Ion exchange resins are commonly used, for example, in the field of water treatment for demineralization of water for boilers or for condensate treatment at power plants, in a food field for purifying a sugar solution or in the field of super pure water for preparation of semiconductors.

In preferred embodiments of the present invention, microparticles are prepared from porous, spherical ion-exchange resins. Spherical ion-exchange resins are made by suspension polymerization, in which a monomer mixture comprising a monofunctional addition-polymerizable monomer and a radical polymerization initiator are added to an aqueous medium, followed by stirring to prepare a suspension of the monomer mixture. The suspension is then maintained at a polymerization temperature for a period of time to obtain a spherical cross-linked copolymer. The diameter of ion-exchange resins for water treatment is typically between 300-600 In other embodiments, microparticles can be prepared from gel type and/or macroporous ion-exchange resins.

Polymer matrices of ion exchange resins may include polystyrene, polystyrene and styrene copolymers, polyacrylate, aromatic substituted vinyl copolymers, polymethacrylate, phenol-formaldehyde, polyalkylamine, combinations thereof, and the like. In a preferred embodiment, the polymer matrix is polystyrene and styrene copolymers, polyacrylate, or polymethacrylate, and in another embodiment the polymer matrix is styrene-divinylbenzene (DVB) copolymers. Preferably, the ion-exchange resin for the preparation of microparticles uses resin which are polystyrene-based, Hydroxyethyl methacrylate (HEMA)-based, dimethylamino ethyl methacrylate (DMAEMA)-based, dimethylamino ethyl methacrylate (pDMAEMA), methacrylic acid (MAA)-based. Most preferably, the resin is made from polystyrene cross-linked with divinylbenzene (DVB).

The cation exchange resin used herein can be weakly or strongly acidic. As used herein, the term "weakly acidic cation exchange resin" refers to a resin having an apparent dissociation constant or ionization constant (pKa) greater than about 4.5 as measured by conventional methods (for example, Fisher et al., "Effect of Cross-linking on the Properties of Carboxylic Polymers. I. Apparent Dissociation Constants of Acrylic and Methacrylic Acid Polymers" J. Phys. Chem., 60(8), 1030 (1956)). It may have the carboxylic acid group, a phenolic hydroxyl group, a phosphonic acid group, and an arsono group as the exchange group. The term "strongly acidic cation exchange resin," on the other hand, refers to a resin having a pKa less than about 1.5. A strongly acidic cation exchange resin may have sulfonic acid groups such as sodium polystyrene sulfonate or polyAMPS. The sulfonic acid group ($—HSO_3$) is the exchange group and behaves like a strong acid, dissociating to ($—SO_3$)$^-$ and $H^+$ in alkaline solutions and even in acidic solutions.

The anion-exchange resin used herein can be weakly or strongly basic. As used herein, the term "weakly basic cation exchange resin" refers to a resin having an apparent dissociation constant or ionization constant (pKa) greater than about 8.5 as measured by conventional methods (for example, Fisher et al., "Effect of Cross-linking on the Properties of Carboxylic Polymers. I. Apparent Dissociation Constants of Acrylic and Methacrylic Acid Polymers" J. Phys. Chem., 60(8), 1030 (1956)). It may have the primary, secondary, and/or ternary amino groups, e.g. polyethylene amine as the exchange group. The term "strongly basic anion exchange resin," on the other hand, refers to a resin having a pKa less than about 12. A strongly basic anion exchange resin may have quaternary amino groups, for example, trimethylammonium groups, e.g. polyAPTAC, or dimethylethanolamine as the exchange group.

Anion-exchange resins and cation-exchange resins used herein further include chelating resins which comprise functional groups that are capable of forming a chelate (complex) with a metal ion. Chelating resins typically feature a great selectivity for specific metal ions. Some chelating resins can be basic and/or acidic, depending on their functional groups and the pH. Typical functional groups of chelating resins include, but are not limited to, iminodiacetic acid, polyamine, methylglucamide, thiouronium, and aminophosphonic acid. AMBERLITE® IRC 748 is an exemplary chelating cation-exchange resin having a functional group of iminodiacetic acid that can be used to prepare microparticles for the recovery of biomolecules from, e.g., a cell suspension.

Commercially available ion exchange resins are for example provided by Rohm & Haas of Philadelphia, Pa., USA as AMBERLITE®, Amberjet, Duolite, and Imac resins, from Bayer of Leverkusen, Germany as Lewatit resin, from Dow Chemical of Midland, Mich. USA as Dow resin, from Mitsubishi Chemical of Tokyo, Japan as DIAION® and Relite resins, from Purolite of Bala Cynwyd, Pensylvania, USA as Purolite resin, from Sybron of Birmingham, N.J. USA as lonac resin, and from Resintech of West Berlin, N.J. USA.

Positively charged microparticles can be prepared from polymeric anion exchange resin. Commercially available anion exchange resins are typically in either OH⁻ or Cl⁻ forms. In one embodiment, the anion exchange resin is in the OH⁻ form. The resin may be for example "DIAION®" anion exchange resins such as DIAION® SA resins (including DIAION® SA 20A) and DIAION® SK resins (including DIAION® SK 110) (from Mitsubishi Chemical) "AMBERLITE®" resins such as AMBERLITE® IRA-400, AMBERLITE® IRA-458, AMBERLITE® IRA-734, and AMBERLITE® IRA-900 (from Rohm & Haas Co.) or "DOWEX®" resins such as DOWEX® 1, DOWEX® 2, DOWEX® 11, DOWEX® 21K, DOWEX® 1×2, DOWEX® 1×4, DOWEX® 1×8 and DOWEX® MARATHON® resins such as MARATHON® A2 (from Dow Chemical Co). In preferred embodiments, the anionic exchange resin is AMBERLITE® IRA-458 or MARATHON® A2. Functional groups in anion exchange resins may include quaternary ammonium groups, e.g., benzyltrimethylammonium groups (type 1 resins), benzyldimethylethanolammonium groups (type 2 resins), trialkylbenzyl ammonium groups (type 1 resins), dimethylethanolamine (type 2 resins) or tertiary amine functional groups. For cell disruption, MARATHON® MA2 and AMBERLITE® IRA-458 are particularly preferred anion exchange resins for the preparation of positively charged micro particles.

Negatively charged microparticles can be prepared from polymeric cation exchange resin. As used herein, a polymeric material may refer to a polymer, a mixture of polymers, a cross-linked polymer, mixtures thereof, or to polymeric networks. Often, a polymeric material is simply referred to as a polymer. Commercially available cation exchange resins are typically in either H⁺ or Na⁺ forms. In one embodiment, a cation exchange resin is in the H⁺ form. The resin may be for example "DIAION®" cation exchange resins such as DIAION® PK resins and DIAION® SK resins (from Mitsubishi Chemical), "AMBERLITE®" resins such as AMBERLITE® IRC-748 (from Rohm & Haas Co.) or "DOWEX®" resins such as DOWEX® 50WX2, DOWEX® 50WX8, and DOWEX® MARATHON® resins such as MARATHON® C, MARATHON® MSC (from Dow Chemical Co). Functional groups of a cation exchange resin may include sulfonic acid groups (—SO₃H), phosphonic acid groups (—PO₃H), phosphinic acid groups (—PO₂H), carboxylic acid groups (—COOH or —C(CH₃)—COOH), combinations thereof. In one embodiment, the functional groups in a cation exchange resin will be —SO₃H, —PO₃H, or —COOH, and in the most preferred embodiment, the functional groups in a cation exchange resin is —SO₃H. For cell disruption, cation exchange resins having a chelating functional group such as AMBERLITE® IRC 748 are particularly preferred for the preparation of negatively charged microparticles.

Polymeric cation exchange resin, as used herein, refers to a polymeric material having one or more elementary charges of the proton, or to such a macromolecule itself. A polymeric anion exchange resin has one or more elementary charges of the electron.

The positively charged microparticles of the invention are particles having at least one elementary charge of a proton, and more typically more than one, at a neutral pH, whereas the negatively charged microparticles have at least one elementary charge of an electron at a neutral pH.

Positively or negatively charged microparticles are obtained when at least a fraction of the constituents of the microparticles are ionically charged.

The present invention also provides as a novel adsorbent material for the capture of biomolecules microparticles which are solid and hydrophobic. The microparticles are in ground form and can be prepared by grinding hydrophobic adsorbent material such as AMBERLITE® XAD4, AMBERLITE® XAD7HP, AMBERLITE® XAD761.

In one embodiment, only positively charged microparticles are added to the biological fluid. In another embodiment, only negatively charged microparticles are added to the biological fluid. Yet in another embodiment, both positively and negatively charged microparticles are added to the biological fluid. If both positively and negatively charged microparticles are added to the biological fluid, the ratio between positively charged microparticles and negatively charged microparticles can be from about 0.1:99.9 (w/w) to 99.9:0.1 (w/w). For example, it can be about 50:50, but it can also be different, such as 90:10, 80:20, 75:25, 60:40, 40:60, 20:80, 25:75, 10:90, etc. In yet another embodiment, hydrophobic microparticles are added to the biological fluid.

In one preferred embodiment, the microparticles are in the form of ground particles having an average particle size less than about 10 such as less than about 9 µm, 8 µm, 7 µm, 6 µm, 5 µm, 4 µm, 3 µm, 2 µm, and 1 µm. Preferably, the ground particles have an average particle size less than about 5 µm, and more preferably less than 2.5 µm. Preferably, the ground particles have an average particle size larger than 0.5 µm. Accordingly, the ground particles may preferably have an average particle size in the range from about 10 µm to 0.5 µm, about 9 µm to about 0.5 µm, about 8 µm to about 0.5 µm, about 7 µm to about 0.5 µm, about 6 µm to about 0.5 µm, about 5 µm to about 0.5 µm, about 4 µm to about 0.5 µm, about 3 µm to about 0.5 µm, or about 2.5 µm to about 0.5 µm. However, the ground particles may have a particle size more than 10 µm as well as less than 0.5 µm.

Preparation of Microparticles

Microparticles are obtainable or obtained by grinding anion-exchange resin and/or cation exchange resin. Preferably, the microparticles of the present invention are obtainable by (or are obtained by) grinding the resin and conditioning the resin.

It is preferable to condition the ground particles to remove residual by-products in the manufacturing process of the resin. Typical conditioning methods for ion exchange resins are well known in the art and also described by the suppliers.

If necessary, "conditioning" can be performed in order to transfer the resin from the H⁺ or OH⁻ to Na⁺ or Cl⁻ form. In one embodiment, conditioning is performed by repeated washing steps using NaCl and water. In the process, the resin can be ground in water and sedimentation can be done by centrifugation. Alternatively, resins already in $Na^+$ or $Cl^-$ form are available commercially and can be obtained from the suppliers.

In a preferred embodiment the microparticles are prepared by (a) grinding the ion exchange resin and (b) resuspending said ground resin in water, (c) allowing sedimentation of said ground resin, (d) collecting ground resin from the supernatant of the sedimented suspension, (e) resuspending collected ground resin in about 2 M sodium chloride, (f) allowing sedimentation of said ground resin, (g) collecting ground resin from the supernatant of the sedimented suspension of (f), (h) allowing sedimentation of said ground resin, (i) collecting the sediment of the ground resin of (h), and (j) washing said collected ground resin.

Hydrophobic microparticles of the present invention are preferably grinded overnight Grinded resins are suspended in water. Supernatant is centrifuged. Resins are re-suspended in salt solution, such as 2 M sodium chloride and centrifuged, a pellet is discarded. Supernatant are transferred and centrifuged again. Supernatant is discarded. Ground resins are re-suspended in water and transferred to tubes. Resins are centrifuged, supernatant is discarded and resin is resuspended in aqueous washing solution. Wash sequence is:

1×50% EtOH (dilution of organic residues)
3× deionized water (dilution of EtOH)

Grinding

Grinding can be carried out in any way known in the art, including, but not limited to, by a grinding device, such as a grinding mill (including a jet mill, a ball mill, a hammer mill or the like), or by hand with for example a mortar and pestle. "Grinding" as used herein refers to an operation leading to a reduction in the particle size. A skilled person can readily select grinding methods to prepare the resins. For example, in one embodiment, the resin is wet ground in an automated manner by moving one or more pestles in a mortar. The grinding process may be continued until the majority of the particles have a size of less than about 10 µm, such as less than 9, 8, 7, 6, 5, 4, 3, 2, 1, 0.5 µm, are obtained. By majority it is meant more than 50%, such as more than 60%, 70%, 80%, 90%, or 95%. In other embodiments, the majority of the particles have an average particle size of at least 0.1 µm, such as 0.2 µm, 0.3 µm, 0.4 µm, 0.5 µm, 0.6 µm, 0.7 µm, 0.8 µm, 0.9 µm, 1.0 µm, 1.1 µm, 1.2 µm, 1.3 µm, 1.4 µm 1.5 µm, 1.6 µm, 1.7 µm, 1.8 µm, 1.9 µm, 2.0 µm, 3 µm, 4 µm or 5 µm.

A skilled person can readily determine the size of ground particles with methods known in the art. From that, the average particle size can be determined by means and methods known in the art. For example, the size can be determined by optical microscopy using a software-based determination of size such as illustrated in the example. Particle size of ground resin can be determined at 1000-fold magnification by estimation of equivalent circular diameters. Distribution is preferably calculated by comparison of diameter sizes of about 100-500 particles at 1% v/v. Grinding has the effect of drastically increasing surface area, which leads to a significant increase in the binding capacity of biomolecules particularly for proteins or polypeptides. Determination of the diameter is preferably done with the aid of technical means such as a software which recognizes a particle and measures the diameter.

"Resuspending" or "suspending" or any grammatical form thereof when used herein means that microparticles are brought into suspension.

"Allowing sedimentation" when used herein means that microparticles are allowed to settle out of the fluid in which they are entrained and come to rest against a barrier. The sedimentation is due to the particles' motion through the fluid in response to forces acting on them. These forces can be gravity or centrifugal acceleration by, e.g., a centrifuge, with the latter being preferred.

"Collecting" means that microparticles are harvested from the suspension.

"Washing" when used herein means that residual amounts of fluids that could disturb or interfere with the performance of the microparticles are reduced. For example, the resins can be washed with 50% (v/v) ethanol (EtOH) and double-deionized water ($ddH_2O$), preconditioned as described above, and subsequently washed repeatedly with $ddH_2O$. The volume of each of these fluids is in excess of the volume of microparticles, preferably 10- or 20-fold in excess.

After the grinding process, particles outside the preferred range can be optionally removed, for example, by centrifugation, sedimentation, filtration, or any other methods known to a skilled person in the art.

Surprisingly, it has been found that the rough surface in the ground particles provides a comparable adsorption capacity for proteins like conventional chromatographic media having high binding capacity such as the Nuvia media developed by Bio-Rad Laboratories (USA).

Addition of the Microparticles

In the first step, the microparticles are added to the biological fluid. The presently disclosed microparticles can be used in laboratory scale, pilot-scale or industrial scale. As used herein, "laboratory scale" comprises batch adsorption of a biomolecule from about 1 or 10 ml fluid to about 1000 ml fluid. As used herein, "pilot-scale" comprises batch adsorption of a biomolecule from about 1 liter fluid to about 10 liter fluid. As used herein, "industrial scale" or large-scale comprises batch adsorption of a biomolecule from about 10 liter fluid to about 1000 or even 10000 or more liter fluid.

The method described herein comprises adding positively charged microparticles, or adding negatively charged microparticles or adding both positively and negatively charged microparticles or hydrophobic microparticles into the biological fluid. If both positively and negatively charged microparticles are added, they can be added as a prepared mixture, or separately, in a simultaneous or successive fashion. If positively and negatively charged microparticles are added successively, i.e. one after another, the present invention thus encompasses first adding the either positively charged microparticles or negatively charged microparticles to the biological fluid, and secondly adding the oppositely charged microparticles to the biological fluid. A skilled person will be able to determine whether only positively charged microparticles or only negatively charged microparticles or both positively and negatively charged microparticles are used considering for example the biological fluid and the desired biomolecule to be recovered from the biological fluid.

In the alternative, the adsorbent according to the present invention comprises hydrophobic resin in the form of ground particles. The outstanding protein adsorption capacities of such hydrophobic microparticles, which are superior to conventional chromatographic media at low salt concentration, are especially useful for e.g. negative purification of polynucleotides or hydrophilic proteins. Accordingly, the present invention provides uses and methods for negative purification of polynucleotides or hydrophilic protein by applying the hydrophobic microparticles. For that purpose To a homogenate or standard protein solution, 50% (v/v) hydrophobic microparticles suspensions are added to homogenate or protein solutions. Microparticles suspensions are incubated, e.g. for 30 minutes. Afterwards microparticles are centrifuged and elution of bound protein is performed by addition of elution buffer, mixing and incubation for e.g. 30 min. Optionally, a second washing step with elution buffer can be included. After elution microparticles are centrifuged again as before. Concentration of protein in supernatants can be quantified by e.g. photometric analysis and purity of target protein can be checked by SDS-PAGE.

The microparticles can be added into the biological fluid from which biomolecules are to be separated. The term "biological fluids" should be understood broadly. They refer to any fluid associated with organisms, such as obtained from or produced by any organisms. Examples of biological fluids include cell culture media, fermentation supernatants, fermentation broths, cell suspensions, cell lysate. Further examples of biological fluids are described herein above. In other embodiments, biological fluids may also be saliva, urine, lymphatic fluid, prostatic fluid, seminal fluid, blood, plasma, sera, sweat, mucous secretion, milk, milk whey, ascites fluid, organ extracts, plant extracts, animal extract. In a preferred embodiment, the biological fluid is any biological fluid described herein, such as a polypeptide or polynucleotide, e.g., plasmid DNA, cosmid DNA, BAC DNA, minicircle DNA, etc. containing fluid, derived from various in vitro or in vivo processes, and particularly, fermentation broth, culture broth, fermentation supernatant, culture supernatant, cell homogenate, cell lysate, or cell suspension. "Cell homogenate" is generally understood as a mixture of broken cells. Cell homogenate may be obtained by a mechanical or chemical method. For example, cells can be homogenized by conventional methods such as high pressure in a homogenizer to render a fermentation homogenate, or by simply mixing in a lysis solution, including alkaline lysis.

Therefore, the present invention also includes a fluid comprising biomolecules and positively and negatively charged microparticles. In preferred embodiments, the biological fluid is agitated during and/or after any of the steps of the methods of the present invention, but preferably not during the step when the particles are allowed to form flocs and/or when the flocs are removed from the biological fluid.

"Cell homogenate" is generally understood as a mixture of broken cells. Cell homogenate may be obtained by a mechanical or chemical method. For example, cells can be homogenized by conventional methods such as high pressure in a homogenizer to render a cell homogenate/lysate, or by simply vortexing the cells in a lysis solution, including alkaline lysis.

Examples of biological fluids include cell cultures, cell homogenates, and cell lysates and fermentation supernatants such as from *E. coli*, and CHO cell culture. The fermentation supernatants or cell homogenates can additionally be filtered, concentrated, dialyzed, conditioned, or treated in another way.

In a preferred embodiment of the present invention, the biological fluid is a cell suspension. The term "cell suspension" as used herein refers to a liquid, such as cell culture medium, buffer, or any other suitable liquid, that comprises preferably intact cells. "Intact" refers to the physical continuity of the cellular membrane enclosing the intracellular components of the cell and means that the cellular membrane has not been disrupted in any manner that would release the intracellular components of the cell to an extent that exceeds the permeability of the cellular membrane under conventional culture conditions.

During and/or after the microparticles are added into the biological fluid, they can be mixed by stirring or shaking (only after the addition of the MPs) to obtain a homogenous mixture. In some embodiments, mixing can enhance flocculation and/or cell disruption by facilitating the contact between cells and/or biomolecules and microparticles. Adsorption takes place spontaneously while the particles are mixed with the biological fluid. However, in some embodiments, no mixing is required after the addition of the microparticles (referred as static incubation in the examples).

Incubation Parameters

When microparticles are added to biological fluid, the optimal volumetric concentration (indicated by "% (v/v)" which refers to the ratio of the respective volumetric fractions) of cells may be adjusted. In some embodiments, the volumetric cell concentration is less than 30 (v/v), such as less than about 25% (v/v), less than about 20% (v/v), less than about 15 (v/v), less than about 10% (v/v), less than about 9% (v/v), less than about 8% (v/v), less than about 7% (v/v), less than about 6% (v/v), less than about 5% (v/v), less than about 4 (v/v), less than about 3% (v/v), less than about 2% (v/v) or less than about 1% (v/v). Mixing may be useful in order to obtain a homogenous mixture of cells and microparticles.

In some aspects of the present invention, the microparticle concentration is preferably less than about 300% (v/v), such as less than about 200%, 100% (v/v), 80% (v/v), 70 (v/v), 60% (v/v), 50% (v/v), 40% (v/v), 30% (v/v), 20% (v/v), 10% (v/v) or less. Selection of volumetric ratios of resin:cells can depend on, for example, microparticle size distributions (effective surface area) and charge densities (functional groups per accessible area).

Flocculation

In some embodiments, the next step after addition of the microparticles to the biological fluid is to allow the formation of flocs. It has been surprisingly found that the microparticles can rapidly form flocs of large diameter with the cells and/or the biomolecules in the biological fluid upon adsorption of the cells and/or the biomolecules to the microparticles.

When the microparticles are added to a cell suspension, cells may be immobilized in flocs by adsorption to the microparticles. In some embodiments, the cells release biomolecules and remain viable. The released biomolecules may or may not adsorb to the micro particles.

When the microparticles are added to a biological fluid, such as a cell lysate or a cell homogenate or a fermentation supernatant, flocs may form upon adsorption of biomolecules to the microparticles. In some embodiments, positively and negatively charged microparticles are first mixed and then added to a biological fluid, and flocculation occurs upon contact of the microparticle mixture with the biological fluid. In other embodiments, first positively or negatively charged microparticles are added to the biological fluid, and subsequently the oppositely charged microparticles are added separately, resulting in the formation of flocs.

In one embodiment the biomolecule is acidic. In this case, positively charged microparticles is added to a biological fluid such as a cell lysate or cell homogenate for adsorption. Positively charged microparticles may also be added to a cell suspension, either at an amount only sufficient to disrupt the cell and to release the biomolecule, or at an higher amount which will disrupt the cell as well as adsorb the biomolecules. A skilled person is able to determine the amount necessary to partially or fully disrupt the cell. Negatively charged microparticles may be added thereafter, which works as cross-linker to increase the particle size and stability of the flocs. Alternatively, negatively charged microparticles such as prepared from chelating cation exchange resin may also be added to the cell suspension at an amount sufficient to disrupt the cell and to release the biomolecule for further purification. Optionally, positively charged microparticles may be afterwards added to increase flocculation.

In another embodiment the biomolecule is basic. In this case, positively charged microparticles may added to a biological fluid such as a cell lysate or cell homogenate to form flocs with the cell debris or other impurities such as DNA, host cell proteins and cell fragments. Negatively charged microparticles may be added to increase the particle size and stability of the flocs, so the flocs can be easily separated and discarded. The basic biomolecules can then be recovered from the supernatant because it would not bind to the positively charged microparticles. Alternatively, positively or negatively charged microparticles may be added to a cell suspension at an amount sufficient to disrupt the cell and to release the biomolecule for further purification. The flocs typically have a size of 100 μm or even larger which makes them visible and facilitates their separation. This means that other unwanted material such as cells and/or cell debris can be easily removed by filtration, rendering centrifugation unnecessary. The present invention is therefore faster and simpler than prior art methods. It is not necessary but possible to regenerate the resin which would otherwise be required if column chromatography was used. Furthermore, the microparticles are a cheap material and thus can be discarded after use.

In preferred embodiments, flocs have an average particle size of at least 5 μm, such as at least 10, 20, 30, 40, 50, 60, 70, 80, 90, 100, 200, 300, 400, 500, 600, 700, 800, 900, 1000 μm, 2000 μm or more are formed.

Adsorption Capacity

The "adsorption capacity" as used herein is defined as the quantity of adsorbed biomolecule (in mg) per ml of resin in equilibrium state. Equilibrium as used herein is the state wherein the rate of adsorption equals the rate of desorption. The adsorption capacity of the microparticles for the desired biomolecule, in particular a soluble polypeptide or polynucleotide, can for instance be determined by quantifying said polypeptide or polynucleotide in the supernatant, for example by fluorescence or spectrophotometry, before and after elution of the biomolecules. The difference of the biomolecule quantity is then considered to be adsorbed to the microparticles. As the person skilled in the art will understand, the adsorption capacity can depend on various parameters, such as characteristics of the microparticles, the biomolecules, pH, temperature, salt concentration, and other parameters, or combinations thereof. In some embodiments, positively charged microparticles can adsorb at least 5 mg, such as at least 6, 7, 8, 9, 10, 15, 20, 25, 30, 35, 40, 45, 50, 55, 60, 65, 70, 75, 80, 85, 90, 95, 100 mg GFP per ml resin under the conditions as set forth in Example 3.1.5. In other embodiments, positively charged microparticles can adsorb at least 5 mg, such as at least 6, 7, 8, 9, 10, 15, 20, 25, 30, 35, 40, 45, 50, 55, 60, 65, 70, 75, 80, 85, 90, 95, 100 mg SOD per ml resin under the conditions as set forth in Example 4.1.3.

Removal of Flocs

Generally, removal of the flocs from a liquid (such as a biological fluid or a buffer) can be performed by filtration, centrifugation, sedimentation, or any other suitable means. A skilled person can readily determine what methods can be used to separate or desorb the flocs from the fluid. The suspension of the flocs can for instance be processed in either a bucket centrifuge (laboratory scale), tubular centrifuge, decanter or disk stack centrifuge for pilot and industrial scale operation. Likewise, it is possible to remove the flocs by filtration where the flocs are retained, or by sedimentation or extraction. Desorption can be achieved by counter-current extraction decanter, mixer-settler or column extractor. Other useful methods for removal may be tangential flow filtration, deep-bed filtration, Dead End Filtration, or methods involving the use of filter press, nutsche filter.

Desorption of Biomolecules

Desorption can be carried out using any methods known in the art. For example, desorption can be carried out by resuspending the flocs in a buffer which allows desorption of biomolecules like proteins (desorption buffer). This can be achieved by using any known means in the art, including a tubular (static) mixer or other mixing devices such as stirred-tank. Desorption can also be achieved by counter-current extraction decanter, mixer-settler or column extractor.

The suspension is then subject to conditions suitable for desorption. A skilled person can readily determine such conditions for desorbing the biomolecules adsorbed on the flocs. Generally, desorption methods used in conventional ion-exchange chromatography can be employed. For instance, desorption can be carried out by elution at a pH below or above the isoelectric point or by increased salt concentration.

The biomolecules can be further purified or enriched by methods known in the art. These include, for example, precipitation, crystallization and/or chromatography selected from the group consisting of hydrophobic interaction chromatography, affinity chromatography, pseudo-affinity chromatography, anion or cation exchange chromatography and/or size exclusion chromatography. Accordingly, the methods described herein include in a preferred embodiment a further step of purifying and/or enriching the desired biomolecule, in particular a protein, by making use of precipitation and/or chromatography.

However, it has been discovered that in some embodiments, the cells can release biomolecules upon interaction with said microparticles without adsorbing to the microparticles. In this case, cells do not adsorb to the microparticles and no flocculation will occur. For example, when charged microparticles are added to a cell suspension of cells carrying an opposite surface net charge, the cells do not adsorb to the microparticles and no flocculation will be observed. The "surface net charge" of a cell is herein defined as the sum of all electric charges present at the cellular surface which may be dependent on the pH of the surrounding solution.

The released biomolecules may or may not adsorb to the microparticles. If the biomolecules do not adsorb to the microparticles, no desorption of biomolecules is carried out. In this case, the biomolecule can be recovered from the supernatant by separating cells and microparticles from the fluid, e.g. by centrifugation or filtration or any other means. If the biomolecules adsorb to the microparticles, desorption is carried out by altering the condition of the microparticles to allow the elution of the biomolecules for example by a desorption buffer. Due to the size of the flocs, after the biomolecules are desorbed by a desorption buffer, it is easy to separate the flocs formed from the desorption buffer.

The person skilled in the art readily knows which methods to apply in order to achieve separation of supernatant from microparticles and/or cells.

Recovery

The present invention can be used to recover biomolecules from a biological fluid and/or cell. Recovering the biomolecule in all its grammatical forms can mean that a biomolecule is obtained, harvested, achieved, received or gained. The biomolecules may be plasmids, polynucleotides or expression products such as peptide, proteins, including proteins that are glycosylated or post-transnationally modified. By means and methods known in the art and/or described herein, the biomolecule may be isolated and/or further processed such as further purified. Moreover, recovery also includes the embodiment that the cells are disrupted to release the biomolecules from the cell, rendering its separation from the cell culture possible. As subsequent steps, further purification and/or enrichment of the biomolecule can be carried out.

Cell Disruption

The present invention further provides a method for cell disruption by adding charged microparticles to a cell suspension. The term "cell disruption" or "disruption of cells" are used interchangeably herein for a method or process for making a cell permeable to such an extent that biomolecules are released from the cell. Cell disruption may or may not involve cell death. Preferably, cell disruption does not involve complete fragmentation of cellular structures, such as the cell wall, resulting in a decrease of cell fragmentation which reduces the level of unwanted contamination including cell debris. In some embodiments of the invention, cells that are disrupted by the method described herein release biomolecules and remain viable. The term "viable" refers to cells which are capable of multiplying under suitable growth conditions.

The released biomolecules may or may not adsorb to the microparticles used to disrupt cells. The biomolecules can subsequently be recovered from the biological fluid using the methods described herein or other known techniques. Thus, the present invention offers a novel method for cell disruption, biomolecule release and subsequent biomolecule recovery in a simplified two-step process. Microparticles of the present invention may be used to open up the cell to release biomolecules so that they could be recovered in the cell suspension, irrespective of the acidity of the biomolecules (i.e. the biomolecule may be acidic, basic or neutral).

Selectivity

The methods of the present invention can provide biomolecules of a higher purity compared to biomolecules obtained by conventional methods of cell disruption. In particular, the methods of the present invention have a higher selectivity than conventional methods used in the prior art due to a lower amount of non-target substances in the recovered biomolecule fraction. A high purity of the recovered biomolecule is favourable because it can obviate the need for further successive purification steps. Preferably, the present methods provide biomolecules with a relative enrichment to non-target biomolecules of more than 30%, such as more than 40%, more than 50%, more than 60%, more than 70%, more than 80%, more than 90%, or even 100%. Methods for assessing the purity of a given biomolecule in comparison to non-target biomolecules are available to the person skilled in the art. For polypeptides, an exemplary method is the quantitative densitometry of proteins stained with Coomassie blue after separation on SDS polyacrylamide gelelectrophoresis (SDS-Page).

When conventional methods for cell disruption are applied, cells are broken and nucleic acids, cell wall components and other fragments are released. Thus, the recovered biomolecules have to be further purified in order to remove the contaminants. However, the methods described herein enable a reduced release of macromolecular contaminants. Such contaminants may include, but are not limited to, dsDNA, RNA, host cell proteins, host cell debris and endotoxins. It has been surprisingly found that the methods of the present invention markedly reduce the dsDNA content up to 2, 3, 4, 5, 6, 7, 8, 9 or 10 times or even more compared to the dsDNA content in a cell homogenate obtained by a standard HPH protocol as described in Example 2.2. The person skilled in the art can determine the dsDNA content in a given sample, for example by fluorimetric or colorimetric assays that are commercially available. Preferably, 5 times less dsDNA is released by the cells when applying the methods of the present invention, and more preferably 10 times less dsDNA, or even less, such as 100 times, or 1000 times less dsDNA is released.

"Endotoxin" as used herein is used interchangeably with lipopolysaccharide (LPS), which is a major constituent of the outer cell membrane of Gram-negative bacteria. Endotoxin is typically released upon destruction of the bacterial outer cell membrane. The methods of the present invention have been surprisingly shown to reduce the amount of released endotoxin compared to the endotoxin content in a cell homogenate obtained by a standard HPH protocol as in Example 2.2. Preferably, 5 times less endotoxin, more preferably 10 times less endotoxin, or even less, such as 100 times, 1000 times, $10^4$ times, $10^5$ or $10^6$ times less endotoxin, is released by the cells when applying the methods of the present invention. The person skilled in the art can readily determine the endotoxin content for example by using the Limulus Amebocyte Lysate (LAL) gel clot test, LAL chromogenic tests and other chromogenic tests that are commercially available or known in the art.

Cultivating Cells which Produce Biomolecules ("the Product")

Prior to applying the adsorbent of the invention, the method of obtaining a biomolecule as defined and described herein may optionally comprise the step of cultivating a (host) cell that produces, such as expresses, a biomolecule (the "product"), preferably an expression product such as a protein or polynucleotide. The term "cultivation of cells" or "culturing of cells" in medium (either with serum or serum free) in the context of the host cells of the present invention refers to the seeding of the cells into the culture vessel, to the growing of the cells in medium until, in case of adherent culturing, a monolayer is formed, or, in case of a suspension culture, a sufficient cell density is established and/or to the maintenance of the cells in medium as soon as the monolayer is formed or to the maintenance of the cells in suspension, respectively. The term "cultivation of cells" or "culturing of cells" in medium also includes that all of the above mentioned steps are performed with serum free medium, so that no or essentially no animal serum products are present during the whole cultivation process of the cells. Cells may be cultivated by exponential feed, or linear or constant feed or other type of feed, fed batch cultivation, or high density cultivation. Yet, in the alternative, the above mentioned steps may also be performed with serum containing medium.

The nucleotide sequence and/or the encoded polypeptide may or may not be heterologous with respect to the cell. By "heterologous," this means derived from a cell or organism with a different genomic background, or is homologous with respect to the (host) cell, but located in a different genomic environment than the naturally occurring counterpart of said nucleotide sequence. This means that, if the nucleotide sequence is homologous with respect to the host, it is not located in its natural location in the genome of said host, in particular it is surrounded by different genes.

In a preferred embodiment of the present invention, the expression product is a proteinaceous product. "Proteinaceous" when used herein refers to any of a group of complex organic macromolecules that contain carbon, hydrogen, oxygen, nitrogen, and usually sulphur and are composed of one or more chains of amino acids. A preferred proteinaceous expression product is a polypeptide. The term "proteinaceous" also means relating to, consisting of, resembling, or pertaining to protein. In a more preferred embodiment of the present invention, the product is a polypeptide of interest which is produced. It is preferred that the product is biologically active. The proteinaceous product may be acidic or basic.

The expression product can be the product of transcription and/or translation of a nucleotide sequence, preferably of a nucleotide sequence that is exogenously added to the cell by means and methods commonly known in the art in the context of genetically engineering host cells. The product can be a nucleotide sequence including, for example, a plasmid, mini-circle DNA, cosmid, BAC, ssDNA or dsDNA sequence or RNA sequence (ribozyme, antisense RNA, sRNA, iRNA, miRNA and the like), all of which are capable of being produced in the cell, or it can be a peptide or polypeptide that is generated by way of translation of the transcribed RNA in the cell.

A "polypeptide" as used herein includes proteins, peptides, polypeptides and fragments thereof, said "polypeptides" all being preferably biologically active. The terms "polypeptide" and "protein" are used interchangeably to refer to polymers of amino acids of any length, generally more than about 10, 20 or 30 amino acids. These terms also include proteins that are post-translationally modified through reactions that include glycosylation, acetylation and phosphorylation. The polypeptide may be a fusion polypeptide fused to a fusion partner for half-life extension, such as Fc-fusions, albumin-fusions, or fusion partners as affinity tag for affinity chromatography, or fusion partners for providing correct N-termini or for increasing production yield of the protein of interest. The term "peptide" refers to shorter stretches of amino acids, generally less than about 30 amino acids. A polypeptide can serve as agonist or antagonist, and/or have therapeutic or diagnostic uses.

Further, a polypeptide expressed in a cell of the present invention can be of mammalian origin although microbial and yeast products can also be produced.

Examples of mammalian polypeptides or proteins include hormones, cytokines and lymphokines, antibodies such as Fabs, nanobodies, dAbs, scFvs, receptors, adhesion molecules, and enzymes as well as fragments thereof. A non-exhaustive list of desired products include, e. g., human growth hormone, bovine growth hormone, parathyroid hormone, thyroid stimulating hormone, follicle stimulating hormone growth, luteinizing hormone; hormone releasing factor; lipoproteins; alpha-1-antitrypsin; insulin A-chain; insulin B-chain; proinsulin; calcitonin; glucagon; molecules such as renin; clotting factors such as factor VIIIC, factor IX, tissue factor, and von Willebrands factor; anti-clotting factors such as Protein C, atrial natriuretic factor, lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A- or B-chain; pro-relaxin; mouse gonadotropin-associated peptide; DNase; inhibin; activin; receptors for hormones or growth factors; integrin; protein A or D; rheumatoid factors; a neurotrophic factor such as bone-derived neurotrophic factor (BDNF), neurotrophin-3,-4,-5, or -6 (NT-3, NT-4, NT-5, or NT-6), growth factors including vascular endothelial growth factor (VEGF), nerve growth factor such as NGF-; platelet-derived growth factor (PDGF); fibroblast growth factor such as aFGF, bFGF, FGF-4, FGF-5, FGF-6; epidermal growth factor (EGF); transforming growth factor (TGF) such as TGF-alpha and TGF-beta, including TGF-p1, TGF-p2, TGF-p3, TGF-p4, or TGF-p5; insulin-like growth factor-I and -II (IGF-I and IGF-11); des (1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha,-beta, and -gamma; colony stimulating factors (CSFs), e.g., M-CSF, GM-CSF, and G-CSF; interleukins (Ls), e.g., IL-1 to IL-10; superoxide dismutase; erythropoietin; T-cell receptors; surface membrane proteins e.g., HER2; decoy accelerating factor; viral antigen such as, for example, a portion of the AIDS envelope; transport proteins; homing receptors; addressins; regulatory proteins; antibodies; chimeric proteins such as immunoadhesins and fragments of any of the above-listed polypeptides.

Preferred polypeptides and proteins herein are therapeutic proteins such as TGF-β, TGF-α, PDGF, EGF, FGF, IGF-I, DNase, plasminogen activators such as t-PA, clotting factors such as tissue factor and factor VIII, hormones such as relaxin and insulin, cytokines such as IFN-y, chimeric proteins such as TNF receptor IgG immunoadhesin (TNFr-IgG) or antibodies such as bispecific antibodies, camelid antibodies and fragments thereof, $V_{HH}$ domain antibodies, domain antibodies, immunoglobulins such as anti-IgG, anti-IgA, anti-IgM, anti-IgD or anti-IgE. Preferred therapeutic proteins are those of human origin or "humanized" proteins such as humanized antibodies as described herein.

If the product is a polypeptide, the polypeptide can be tagged, i.e., fused with a heterologous polypeptide which preferably allows isolation and/or purification of said polypeptide. The heterologous polypeptide can, for example, be a histidine tag, Flag-tag, streptavidin tag, strep II tag, an intein, maltose-binding protein, an IgA or IgG Fc portion, protein A or protein G.

If the product is a polynucleotide including a nucleotide sequence, the nucleotide sequence may be fused with a heterologous nucleotide sequence which allows isolation and/or purification of said expression product being a nucleotide sequence. For example, the heterologous nucleotide sequence can bind to a complementary nucleotide sequence, thereby allowing isolation and/or purification of said nucleotide sequence. "Heterologous" when used in the context of a heterologous polypeptide or nucleotide sequence means that a polypeptide or nucleotide sequence is different from the polypeptide or nucleotide sequence being the desired expression product.

If the product, as an example of a polynucleotide, is a plasmid, said plasmid is useful for gene therapy or DNA vaccination, or may encode a therapeutic protein, such as one described herein.

On the other hand, the cell may express a virus, i.e., the host cell serves as producer cell line that provides, so to say, the appropriate environment that the virus replicates and/or is propagated. Accordingly, the product could be a virus. Virtually, any virus can be recovered by the methods of the present invention such as dsDNA viruses (e.g. Adenoviruses, Herpesviruses, Poxviruses), ssDNA viruses (e.g. Parvoviruses), dsRNA viruses (e.g. Reoviruses), (+) ssRNA viruses (e.g. Picornaviruses, Togaviruses), (−) ssRNA (e.g.

Orthomyxoviruses, Rhabdoviruses), ssRNA-RT viruses (e.g. Retroviruses) and dsDNA-RT viruses (e.g. Hepadnaviruses). Viral replication is the term used to describe the formation of virus during the infection and propagation process in the target cells. From the perspective of the virus, the purpose of viral replication is to allow production and survival of its kind. By generating abundant copies of its genome and packaging these copies into viruses, the virus is able to continue infecting new hosts. In the context of the present invention it is preferred that viruses produced by appropriate host cells are not or essentially not capable of exiting the host cell, for example, by way of lysis or budding.

As mentioned before, the product may also be a virus. A "virus" includes "native" viruses and "recombinant" viruses, with "native" meaning a virus which is isolated from nature and not genetically engineered (such as a clinical isolate) or a virus which can be found in nature (i.e., naturally-occurring) or a typical, established virus strain, for example used for immunization purposes (such as an attenuated virus).

In sum, the present invention provides a fast, efficient, simplified and inexpensive method which can be easily applied on an industrial scale.

EXAMPLES

Example 1: Preparation of Micro Particles from Ion Exchange Resins

Resin beads for water treatment were purchased from DOW. An overview of tested resins is shown in Table 1.

TABLE 1

| | Resin | | | | | |
|---|---|---|---|---|---|---|
| | Matrix | | | Function | Exchanged | |
| Name | Polymer | Type | Group | Type | ion | Capacity |
| MARATHON ® MSC | Styrene-DVB | Macroporous | Sulfonic acid | Strong acid | Cation | ≥1.7 (Na) |
| MARATHON ® A2 | Styrene-DVB | Gel | Dimethylethanol ammonium | Strong base | Anion | ≥1.2 (Cl) |
| AMBLERLITE ® IRC748 | Styrene-DVB | Macroporous | Iminodiacetic acid | Chelating | Cation | ≥1.25 (Na) |
| AMBLERLITE ® IRA458 | Acrylic | Gel | Trimethyl ammonium | Strong base | Anion | ≥1.25 (Cl) |

All resins were preconditioned to their sodium or chloride form for cation exchangers (MARATHON® MSC, AMBERLITE® IRC748) and anion exchangers (MARATHON® A2, AMBERLITE® IRA458), respectively. Afterwards particles were repeatedly washed with deionized water (<1 mS/cm and pH neutral). An overview of functional groups of resins is showed in FIG. 1.

Microparticles were wet ground at the company NETSCH with a Labstar LS1 mill or manually with a pestle and mortar. An overview of average particle size distribution (PSD) obtained by grinding is shown in Table 2. Particle sizes were measured by optical microscopy at 1000× magnification and average equivalent circular diameter was estimated by counting 500-50000 discrete projections.

TABLE 2

| Particle size distributions | | |
|---|---|---|
| Resin | Size d50 (μm) | Distribution d1-d99 (μm) |
| MARATHON ® MSC | 0.9 | 0.4-1.9 |
| MARATHON ® A2 | 1 | 0.4-2.4 |
| AMBERLITE ® IRC748 | 1 | 0.2-4.5 |
| AMBERLITE ® IRA458 | 1.4 | 0.4-5.1 |

Shapes of ground particles from optical projections were considered undefined. Suspensions concentration was adjusted by centrifugation and estimated from packed bed volume in deionized water. Water content was calculated from weight difference of wet and dried resin.

Example 2: Recovery of Target Proteins

Example 2.1 Recovery of Target Proteins by CSPE

E. coli (HMS174) cells were cultivated in fed batch at 37° C. (GFPmut3.1) and 30° C. (SOD). Expression of recombinant protein was IPTG induced. Cells were collected by centrifugation. Protein extraction experiments were performed with aliquots at room temperature. Initially volumetric cell concentration (wet packed bed) was approximately 10% v/v. This was determined by centrifugation of 50 ml suspensions at 4000 rcf for 10 min. For experiments with various cell and salt concentrations, pellets were suspended by vigorous mixing in respective buffer. Final cell, particle, buffer and salt concentrations were adjusted by adding 10× stock solutions to 50% suspensions and dilution with ddH2O to working volume (20 ml). Incubation was performed for up to 3 hours at room temperature (~23° C.) in stirred beakers (mixing) or in tubes (static). Both had similar height to diameter ratios. Mixing intensity was adjusted to 800 rpm with a convenient magnetic stirrer at bottom. For quantification of released protein aliquots of 1 ml were diluted 1:2 with respective buffer. Samples were centrifuged thereupon at 8000 rcf for up to 10 min (~23° C.) and supernatants collected for further investigations.

Example 2.2 Extraction of Target Proteins by HPH

E. coli (HMS174) cells were cultivated in fed batch at 37° C. (GFPmut3.1) and 30° C. (SOD). Cell were suspended in buffer (50 mM Tris, pH 8.0, 100 mM NaCl) to 25% v/v and disrupted by high pressure homogenisation (Niro-Soave Panda 2k, 2× passes at 100 MPa).

Example 3: Quantification of Target Proteins by Fluorescence

Example 3.1 Fluorescence

GFPmut3.1 standard (>95%) was prepared by sequential purification from clarified *E. coli* homogenate (centrifuged for 60 min at 10000 rcf and 0.2 micro filtered) with anion exchange (AIEX CaptoQ), hydrophobic interaction (ButylSepharose) and gel filtration (SuperdexG75 prep. grade) chromatography. Concentration was determined from absorbance at 280 nm (denatured in 8M Urea, 10 min at 100° C.). Equivalent fluorescence was determined from standard calibration at 485 nm (excitation) and 535/20 nm (emission) on plate reader (Tecan GENios Pro).

Recovery efficiency (% Recovery) of GFP was quantified relative to HPH cell disruption (2 passages at 100 MPa as described in Example 2.2).

Example 3.1.1 Cell Concentration

The recovery of GFP from *E. coli* cells recovered by adsorption on ground MARATHON® A2 (MA2) and elution with NaCl was determined. Cells were separated from cell broth by centrifugation and suspended in 50 mM TRIS at pH 8.0 at volumetric concentrations of 20% (v/v), 6% (v/v), and 1% (v/v). Cell suspension was mixed with various volumetric ratios of resin 200%, 100%, 50% and 0% and incubated statically for 1 h. Elution was performed by 1:2 dilutions of suspensions aliquots with 2M NaCl. GFP in aqueous phase was quantified by fluorescence. Ground MARATHON® MSC (MMSC) was used at same conditions for comparison with cationic resin.

Figure 2:
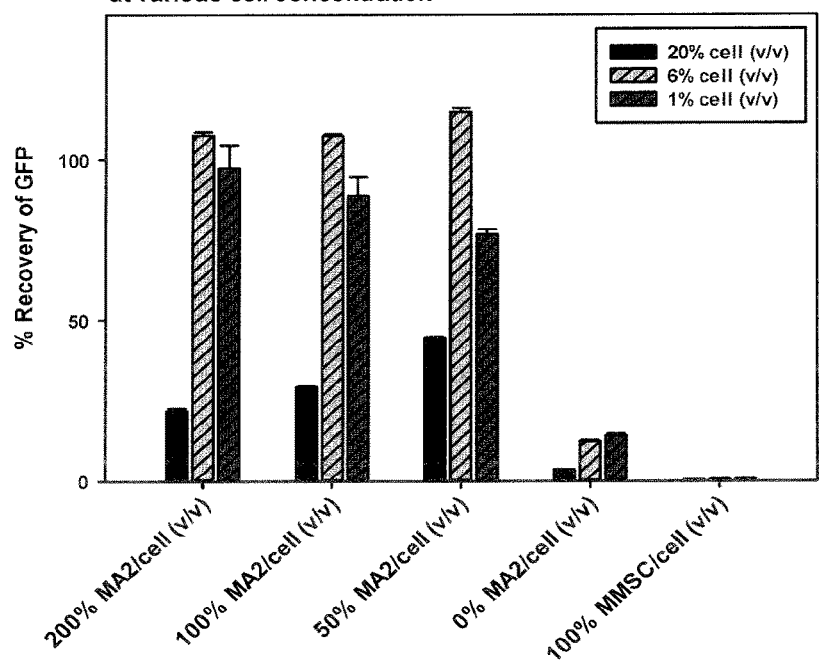
FIG. 2: Influence of the volumetric cell concentration and volumetric resin:cells ratio of MARATHON® A2 microparticles on GFP recovery from GFP expressing E. coli at 1 hour incubation (50 mM TRIS, pH 8.0).

FIG. 2 shows that at 6% (v/v) cell concentration a GFP recovery of 100% was achieved. At 20% (v/v) cell concentration the amount of extracted protein decreased below 50%. In contrast, adding lower amounts of microparticles to 20% (v/v) cell suspension resulted in higher recovery, up to 45%. At 1% amount of recovered GFP decreased proportionally with amount of microparticles. With no microparticles added, amount of GFP in supernatants was below 20%. No effect of protein extraction and cell disruption could be observed by incubation of cells with ground MARATHON® MSC (cation exchanger) at same conditions.

Example 3.1.2 Volumetric Ratio of Resin:Cells

The recovery of extracted GFP from *E. coli* cells recovered by adsorption on ground MARATHON® A2 (MA2) and elution with NaCl at different volumetric ratio of resin:cells was determined. Cells were separated from cell broth by centrifugation and suspended in 50 mM TRIS at pH8.0 at 10% (v/v). The cell suspension was mixed with various volumetric ratios of resin 200%, 100%, 70%, 50%, 30% and 0% and incubated statically for 1 h. Elution was performed by 1:2 dilutions of suspensions aliquots with 2M NaCl. GFP in aqueous phase was quantified by fluorescence.

Figure 3:
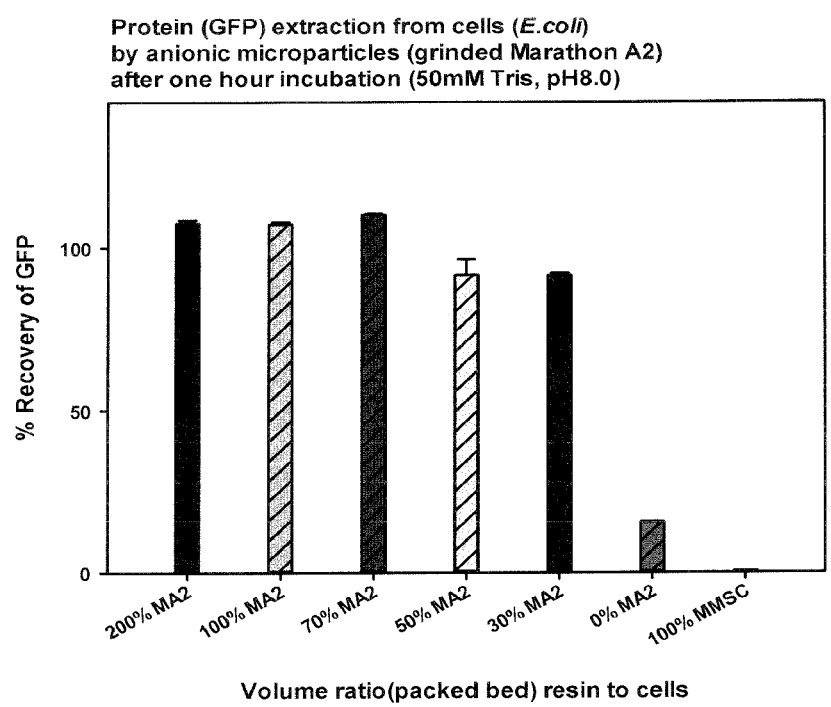
FIG. 3: Influence of the volumetric resin:cells ratio of MARATHON® A2 microparticles on GFP recovery from GFP expressing E. coli (10% v/v) at 1 hour incubation (50 mM TRIS, pH 8.0).

FIG. 3 shows that after one hour of incubation, almost 100% of GFP was recovered by desorption from ground MARATHON® A2. Less than 20% of total soluble GFP was extracted from cells without MARATHON® A2.

Example 3.1.3 pH and Incubation Time

The recovery of extracted GFP from *E. coli* cells recovered by adsorption on ground MARATHON® A2 (MA2) and elution with NaCl at different pH values and different incubation times was determined. The pH of cell broth suspensions was adjusted to 7.5, 8.0 and 8.5 by adding NaOH. Cell suspension was mixed with a volumetric ratio of 100% of resin and incubated statically for 3 h. Periodically (10, 60, 120, 180 min) elution was performed by 1:2 dilutions of suspensions aliquots with 2M NaCl. GFP in aqueous phase was quantified by fluorescence. After a maximum incubation time of 3 h approx. 40% and 70% of total soluble GFP could be recovered at pH 7.5 and 8.0 from cell broth. 100% recovery was achieved only at pH8.5.

Example 3.1.4 pH, Volumetric Ratio Resin:Cells and Incubation Time

The influence of the volumetric resin:cell ratio between 0-100% was further investigated. The pH of cell broth suspensions was adjusted to 7.5, 8.0 and 8.5 by adding NaOH. Cell suspension was mixed with various volumetric resin:cell ratios of 100%, 70%, 50%, 30% and 0% and incubated statically for 3 h. Periodically (10, 60, 120, 180 min) elution was performed by 1:2 dilutions of suspensions aliquots with 2M NaCl. GFP in aqueous phase was quantified by fluorescence.

Figure 4A:
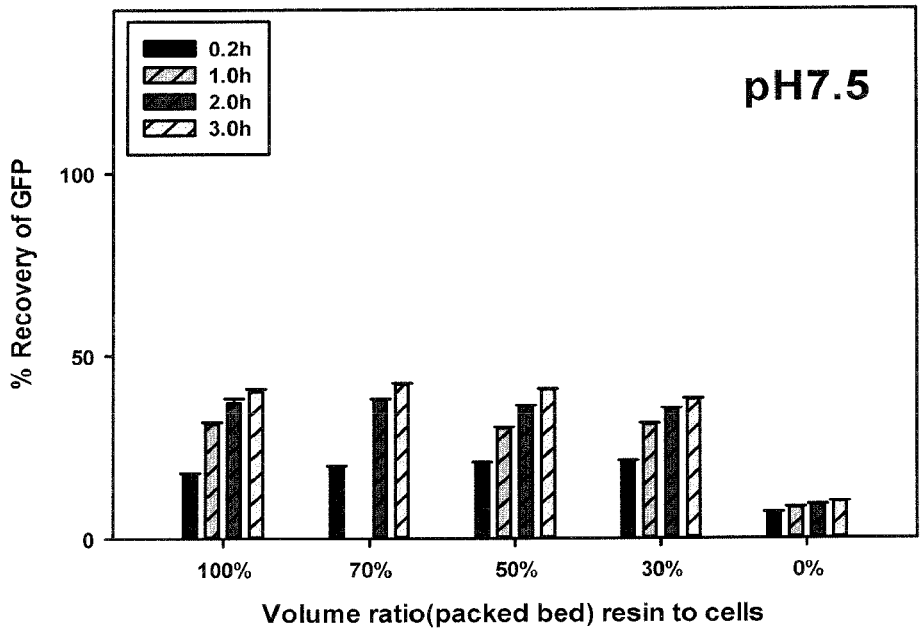
FIG. 4A is a graph showing the extraction kinetic of MARATHON® A2 microparticles on GFP recovery from cell broth containing GFP expressing E. coli after incubation at pH 7.5.
Figure 4B:
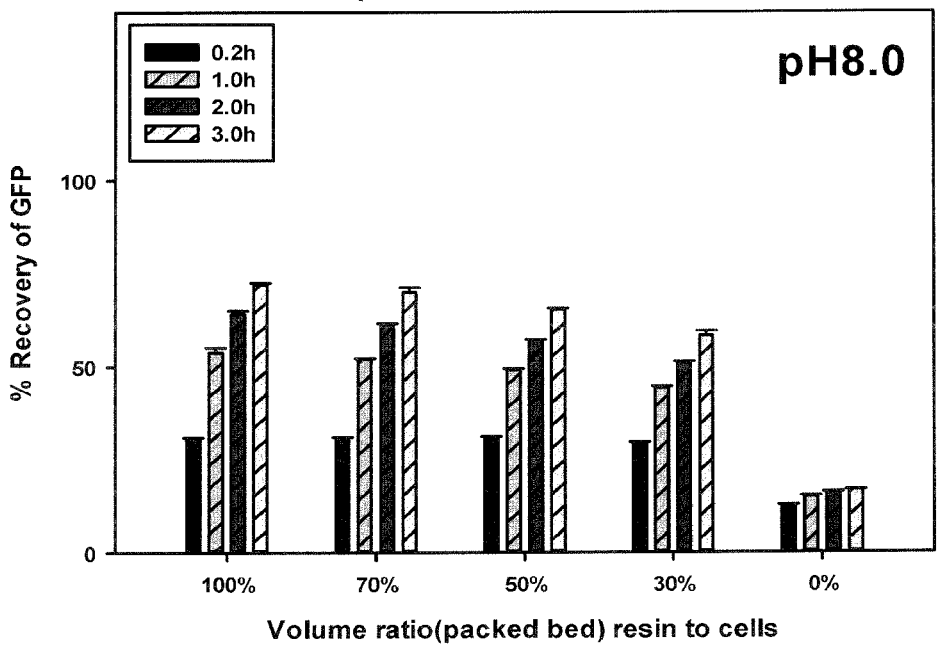
FIG. 4B is a graph showing the extraction kinetic of MARATHON® A2 microparticles on GFP recovery from cell broth containing GFP expressing E. coli after incubation at pH 8.0.
Figure 4C:
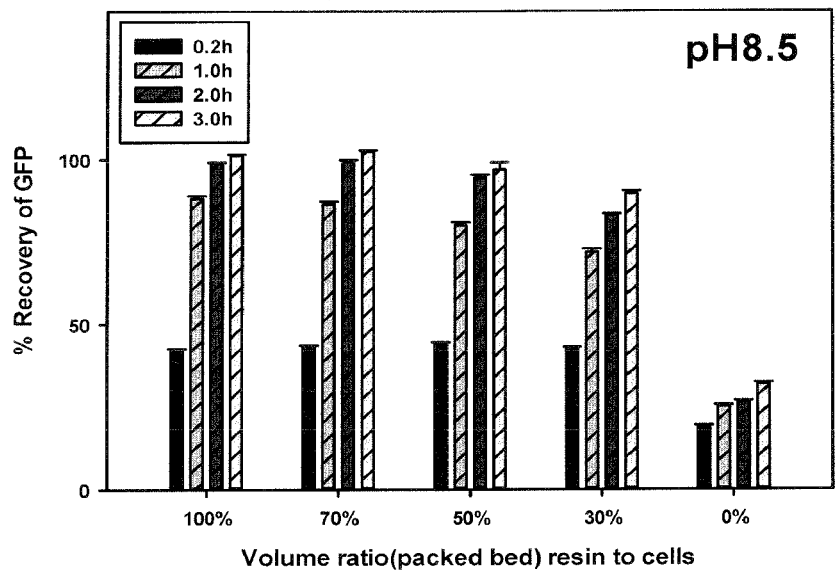
FIG. 4C is a graph showing the extraction kinetic of MARATHON® A2 microparticles on GFP recovery from cell broth containing GFP expressing E. coli after incubation at pH 8.5. All experiments were performed using a 0.2-3 hour static incubation with the microparticles.

FIGS. 4A-4C show that while the pH had a significant influence on the maximum recovery, the effect of added resin amount was negligible. 70% resin:cells ratio (v/v) at pH 8.5 after 2 hours of static incubation was considered to be efficient for disruption of 10% (v/v) of cell suspension and recovery of GFP directly from cell broth.

Example 3.1.5 Salt Concentration and GFP Adsorption Capacity

The recovery of extracted GFP from *E. coli* cells recovered by adsorption on ground MARATHON® A2 (MA2) and elution with NaCl at different NaCl concentrations (0-500 mM) was determined. Cells were separated from cell broth by centrifugation and suspended in 50 mM TRIS at pH8.0 at 10%, v/v. NaCl concentration of suspensions was adjusted with 2M NaCl buffer solution. Cell suspension was mixed with various volumetric ratios of 100%, 70%, 50%, 30% and 0% of resin:cells and incubated statically for 1 h. Elution was performed by 1:2 dilutions of suspensions aliquots with 2M NaCl. GFP in aqueous phase was quantitated by fluorescence.

Figure 5:
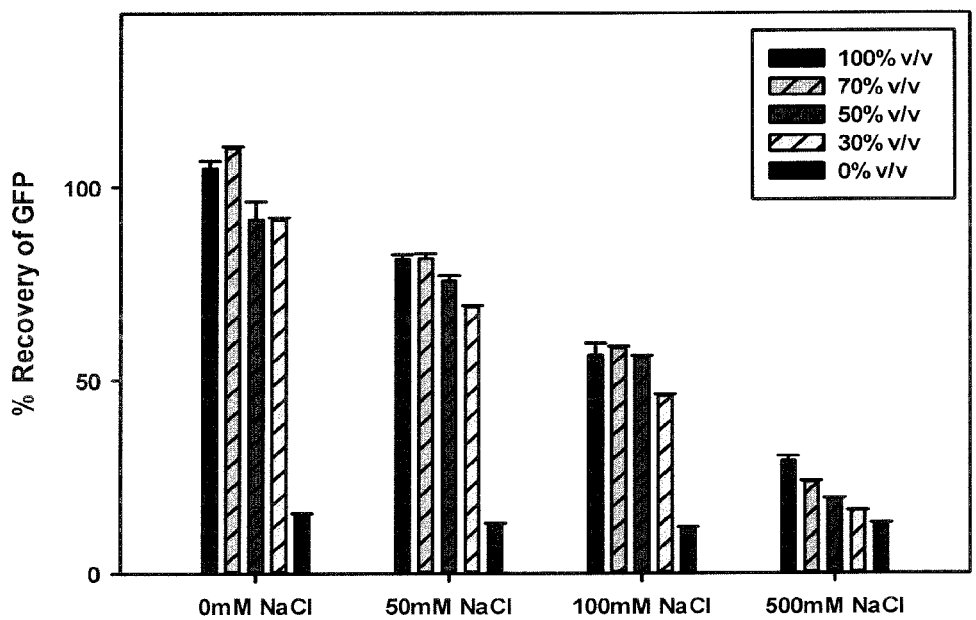
FIG. 5: Influence of salt concentration on recovery of GFP from GFP expressing E. coli (10% v/v) after 1 h incubation (50 mM TRIS, pH 8.0) with MARATHON® A2 microparticles (100%, 70%, 50%, 30%, 0% volumetric ration of resin:cells) and different NaCl concentrations (500 mM, 100 mM, 50 mM, 0 mM) and elution in 1 M NaCl.

FIG. 5 shows that up to 100% GFP recovery was achieved at 0 mM NaCl.

Figure 6:
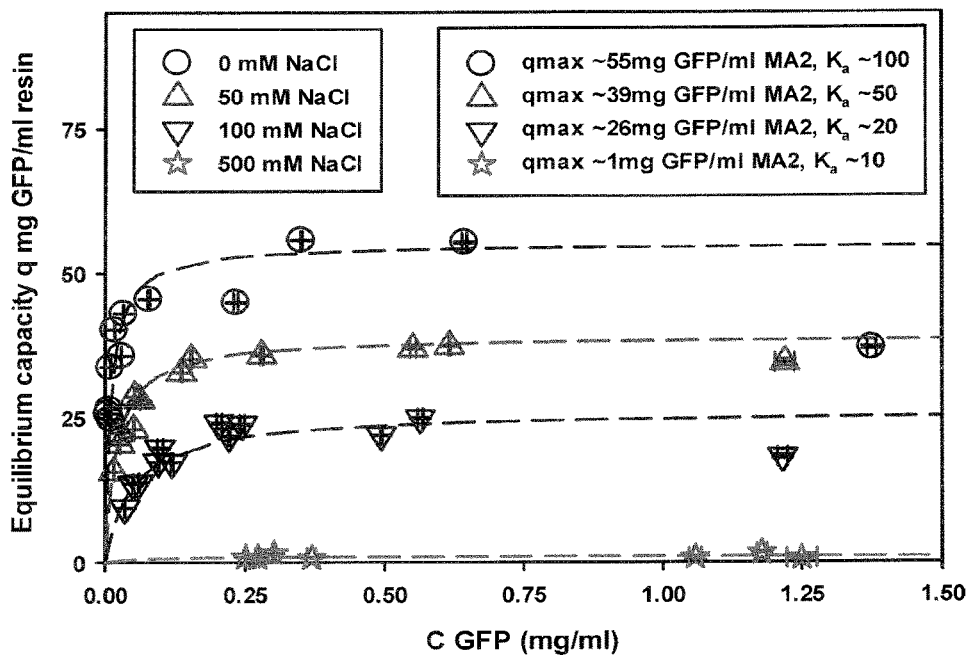
FIG. 6: Equilibrium capacities of GFP extracted from E. coli cells (10% v/v) by adsorption on MARATHON® A2 microparticles (100%, 70%, 50%, 30%, 0% volumetric ratio resin:cells) after static incubation (50 mM TRIS, pH 8.0) in different NaCl concentrations (500 mM, 100 mM, 50 mM, 0 mM) and elution in 1 M NaCl. GFP from aqueous phase was quantified by fluorescence before and after elution in 1M NaCl. Difference of GFP quantity was considered to be adsorbed on resin. Trends were fitted with the standard "Langmuir" equation.

The amount of GFP bound to microparticles was investigated by comparison of concentration in aqueous phase (supernatant) before and after desorption (FIG. 6). The difference of GFP quantity was considered to be adsorbed to resin. Trends were fitted with the standard Langmuir equation.

Example 3.1.6 Extraction with Anionic Chelating Resin

Figure 7A:
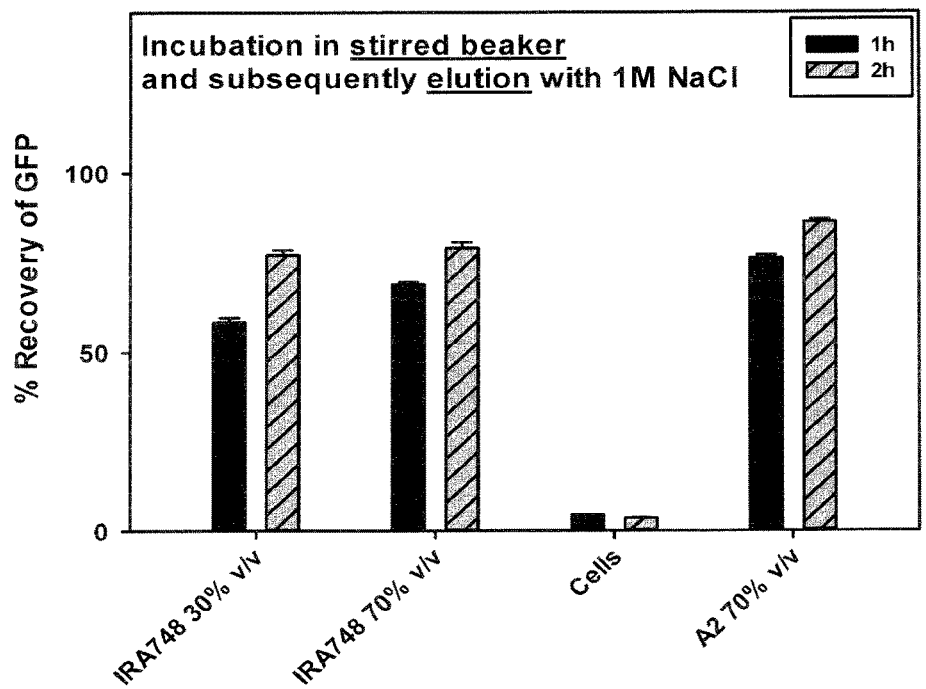
FIG. 7A: Influence of incubation conditions on recovery of GFP from GFP expressing E. coli (5% v/v) after stirring (1-2 hours, 50 mM TRIS, pH 8.0) with chelating AMBERLITE® IRC 748 microparticles (70%, 30% volumetric ratio of resin:cells) with elution in 1 M NaCl.
Figure 7B:
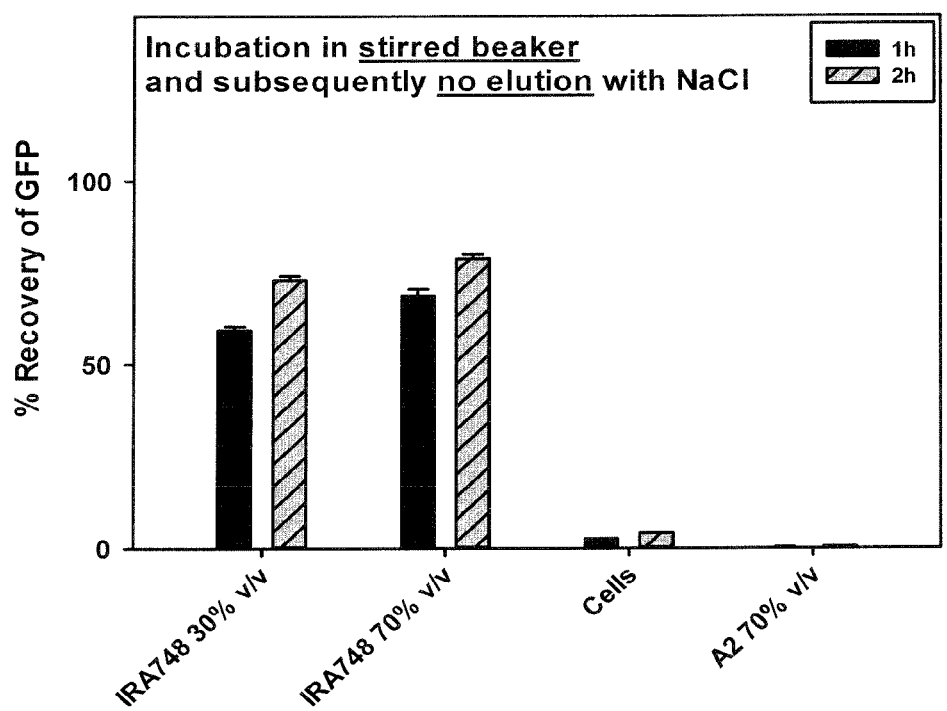
FIG. 7B: Influence of incubation conditions on recovery of GFP from GFP expressing E. coli (5% v/v) after stirring (1-2 hours, 50 mM TRIS, pH 8.0) with chelating AMBERLITE® IRC 748 microparticles (70%, 30% volumetric ratio of resin:cells) without elution in 1 M NaCl.

Protein extraction was also demonstrated from incubation of *E. coli* cells with chelating microparticles (FIGS. 7A-7B). In contrast to strongly basic quaternary groups of MARATHON® A2, iminodiacetic acid groups of self-made microparticles from AMBERLITE® IRA 748 are cation exchangers with high affinity to multivalent cations. In that case no flocculation of suspension had been observed.

GFP extraction from cell suspension (*E. coli*) with chelating (ground AMBERLITE® IRA 748) and cationic microparticles (ground MARATHON® A2) was determined after incubation in 50 mM TRIS buffer at pH8.0 at 30% and 70% v/v volume ratios of resin:cells (5% v/v) and subsequent elution with 1M NaCl and compared to GFP extraction under the same conditions without elution with salt (FIGS. 7A-7B). Further, GFP extraction under stirring and static incubation conditions was determined (FIGS. 7A-7B). GFP was not adsorbed on chelating microparticles in contrast to ground MA2 wherein protein had been recovered by desorption. The protein yield from seems not to be influenced by static or stirring conditions during incubation with chelating microparticles at performed scale.

Example 3.1.7 Influence of Elution Conditions on Protein Extraction

Figure 8:
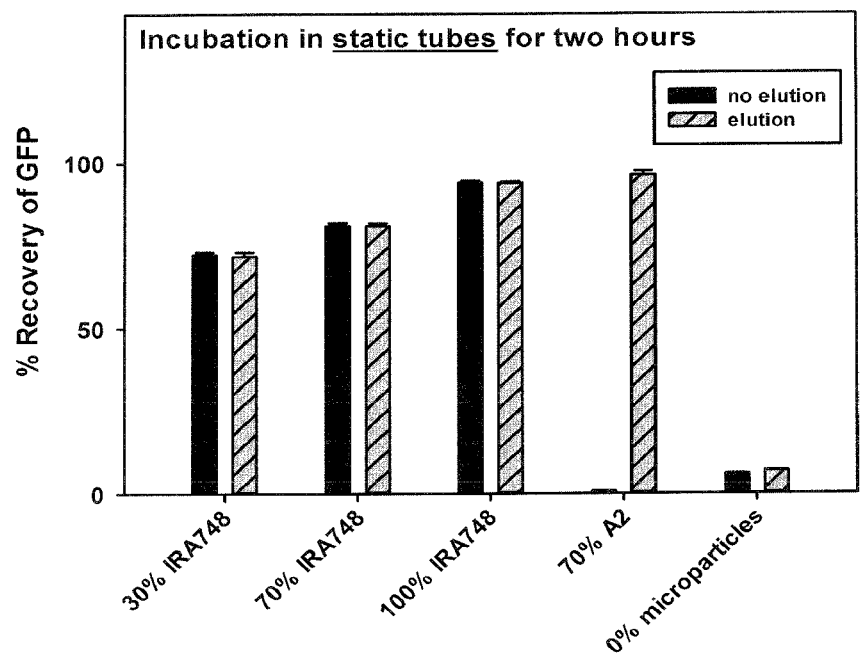
FIG. 8: Influence of volumetric resin:cells ratio and elution on GFP recovery from GFP expressing E. coli (5% v/v) after 2 hour static incubation (50 mM TRIS, pH 8.0) with chelating AMBERLITE® IRC748 microparticles (100%, 70%, 30% volumetric resin:cells ration) and with or without elution in 1 M NaCl.

GFP extraction from cell suspension (*E. coli*) with chelating (ground AMBERLITE® IRA 748) and cationic microparticles (ground MARATHON® A2) was determined after static incubation for 2 hours in 50 mM TRIS buffer at pH8.0 at 30%, 70% and 100% v/v volume ratios of resin:cells (5% v/v) and subsequent elution with 1M NaCl and compared to GFP extraction under the same conditions without elution with salt. GFP extraction yields up to 100% were obtained by incubation of *E. coli* cells for 2 hours at pH 8.0, 50 mM TRIS with ground AMBERLITE® IRA 748 (FIG. 8). The yield of recovered GFP increased with volumetric ratio of chelating microparticles added.

Example 3.1.8 Influence of Cell Concentration on Protein Extraction

Figure 9:
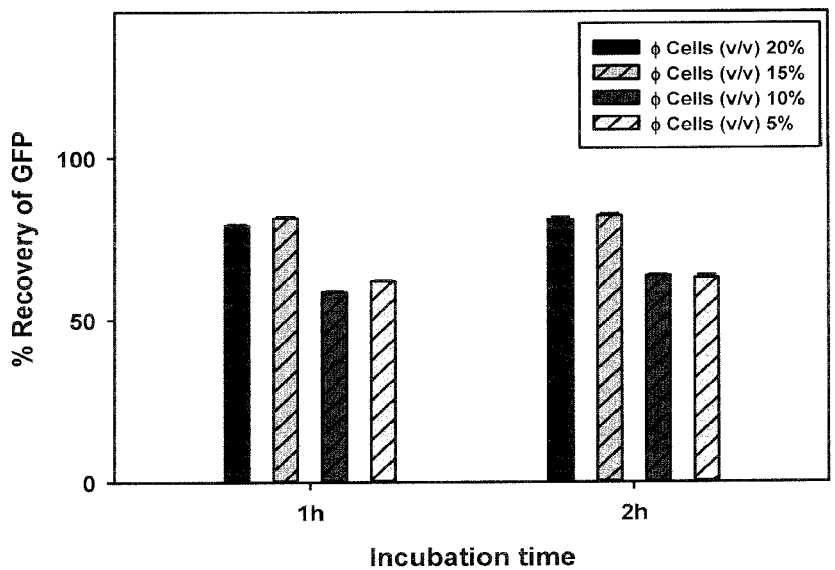
FIG. 9 Influence of volumetric cell concentration (20%, 15%, 10%, 5% v/v) of GFP expressing E. coli on GFP recovery after 2 hour stirring incubation (50 mM TRIS, pH 8.0) with chelating AMBERLITE® microparticles (70% volumetric resin:cells ratio).
Figure 10:
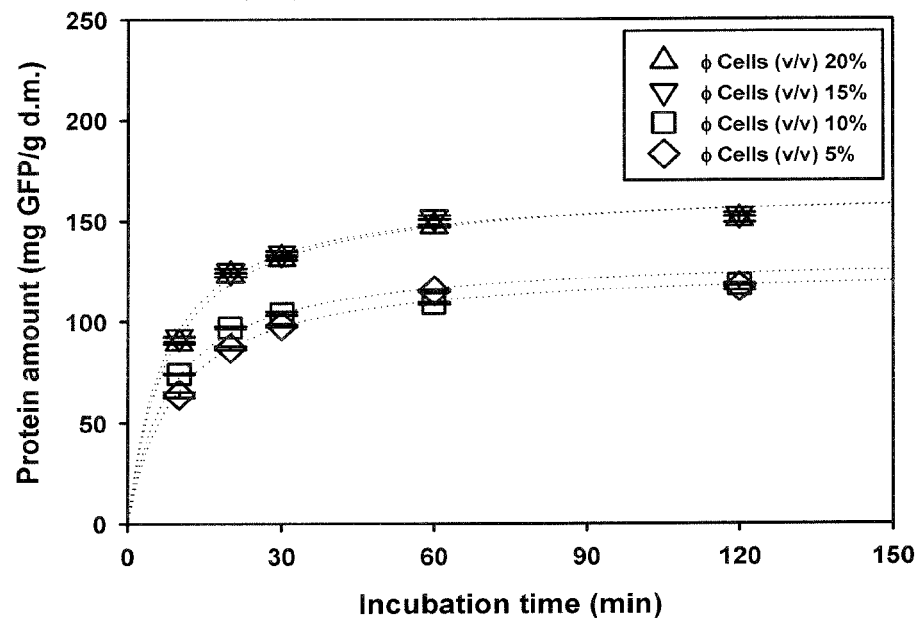
FIG. 10: GFP extraction kinetic of GFP expressing E. coli at different volumetric cell concentrations (20%, 15%, 10%, 5% v/v) after 2 hour stirring incubation (50 mM TRIS, pH 8.0) with chelating AMBERLITE® microparticles (70% volumetric resin:cells ratio).

Protein (GFP) extraction from cell suspension (*E. coli*) with chelating resin (ground AMBERLITE® IRA 748) was determined after incubation in 50 mM TRIS buffer at pH 8.0 in stirred beakers with 70% v/v volume ration of resin:cells at 20%, 15%, 10% and 5% volumetric cell concentration and no elution with salt (FIG. 9). Higher cell concentrations in suspension favourably influenced the extraction yield for chelating miroparticles. A GFP extraction kinetic of extracted protein amount in relation to dry biomass (d.m.) of *E. coli* was determined (FIG. 10).

Example 4: Quantification of Target Proteins by SDS Page

Heavy solid fraction of *E. coli* homogenate was separated by centrifugation at 4000 rcf for 15 min. Supernatant was transferred and light fraction was collected after 60 min centrifugation at 4000 rcf. Pellet was suspended in deionized water and washed sequentially two times as before. Reference samples of cell debris and crude homogenate were diluted 1:5 with 10M Urea, pH 8.0 and incubated for one hour on a rotatory shaker.

All samples were heated for 10 minutes at 100° C. in 1:4 SDS Sample buffer and 0.2M DTT. Electrophoresis was performed on 8-12% polyacrylamide gels in MES-SDS running buffer at 200V and a maximum of 400 mA for 60 minutes. Staining was performed with CoomassieR250 and BismarkBraunR (Choi et al. 1996). Densitometry was performed by optical gel scanning (Epson Perfection Scan V770, 600 dpi, 16 bit grayscale) and evaluation with Lumi-Analyst (v3.0 Roche Diagnostics) software.

Example 4.1 SOD Extraction

Protein extraction was demonstrated from incubation of *E. coli* cells with cationic microparticles obtained from AMBERLITE® IRA458. In contrast to styrene divinylbenzene (PS/DVB) matrix of MARATHON® A2, microparticles obtained from acrylic resin contained more water at same packed bed volume. Flocculation was apparently stronger with acrylic microparticles (bigger flocks and faster sedimentation) but this was not investigated in detail. Additionally target protein was superoxide dismutase (SOD) instead of GFP.

Example 4.1.1 Protein Yield at Varying Incubation Conditions

Protein (SOD) extraction yield was determined from cell suspension (*E. coli*) with acrylic resin (ground AMBERLITE® IRA458) after static incubation in 50 mM TRIS buffer at pH8.0 in tubes at 50, 70 and 100% v/v volume ratio of resin:cells (10% v/v) and subsequent elution with NaCl. Protein amount was estimated by densitometry from standard calibration on SDS-Page (FIGS. 11A-11D). The kinetic of SOD release was almost finished after 1 hour of static incubation with acrylic resin. SOD adsorbed to acrylic microparticles was recovered with 0.5 M and 1.0 M NaCl to an equal amount.

Example 4.1.2 SOD Recovery from *E. coli* Homogenate

Figure 12:
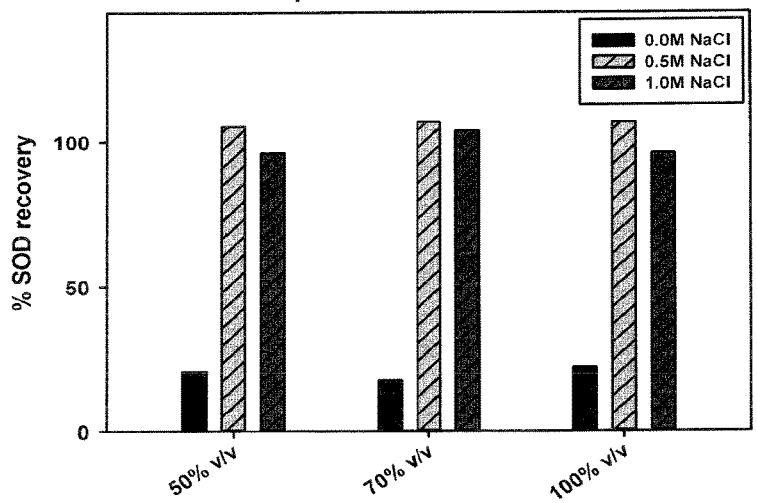
FIG. 12: Recovery of SOD from E. coli homogenate obtained from 10% v/v cell suspension after short mixing and incubation (50 mM TRIS, pH 7.7) with acrylic AMBERLITE® IRA 458 microparticles (100%, 70%, 50% v/v resin:cells ratio) and elution with different NaCl concentrations (1.0 M, 0.5 M, 0 M). SOD amount was determined by SDS-Page densitometry.

Recovery of SOD from *E. coli* homogenate obtained from 10% (v/v) cell suspension was determined after incubation with AMBERLITE® IRA 458 microparticles (100%, 70%, 50 v/v volumetric resin:cells ratio) after short mixing and incubation (50 mM TRIS, pH 8.0) and subsequent elution with NaCl (0.0 M, 0.5 M, 0.1 M). SOD adsorbed to AMBERLITE® IRA 458 microparticles was recovered in equal amounts at elution in 0.5 M and 1.0 M (FIG. 12).

Example 4.1.3 SOD Adsorption Capacity

The amount of SOD bound to microparticles was investigated.

SOD standard (>95% appreciated by Coomassie staining of SDS-Page) was prepared by extraction from *E. coli* cells with A2 microparticles and desorption after 2 h of incubation at 70% v/v (resin/cells) in 50 mM TRIS buffer at pH 8.0 with 0.2M NaCl and subsequently purified by gel filtration (SuperdexG75 prep. grade from GE). Concentration was determined from absorbance at 280 nm (denatured in 8M Urea, 10 min at 100° C.). Concentration of samples was evaluated by densitometry from 5 point calibration on SDS-page. Concentrations of SOD samples obtained by extraction and homogenization were compared by integration relatively to standard.

Example 5: Non-Target Protein Extraction

Purity of extracted GFP by adsorption on ground MARATHON® A2 was checked by SDS-Page in comparison with homogenate. After HPH the heavy solid fraction (containing e.g. GFP inclusion bodies) of *E. coli* homogenate was separated by centrifugation at 4000 rcf for 15 min. Supernatant was transferred and light homogenate fraction was collected after 60 min centrifugation at 4000 rcf. The light homogenate fraction contains cell debris and membrane proteins such as outer membrane protein A (OmpA) and acts as an indicator of cell disruption. Pellet was suspended in deionized water and washed sequentially two times as before. Reference samples of cell debris and crude homogenate were diluted 1:5 with 10M urea, pH 8.0 and incubated for one hour on a rotatory shaker. SDS-Page was performed with crude homogenate, homogenate supernatant and eluted protein extracted by incubation of cells with 50% v/v ground MARATHON® A2 at pH8.0 for 3 h in 50 mM TRIS. Aliquots of suspension were eluted by 1:2 dilutions in 200, 250, 300, 350, 400, 450, 500 and 1000 mM NaCl. SDS-Page of all samples was performed at same dilution ratio and densitometry of Coomassie staining was used for appreciation of protein amounts. Washed cell debris was applied as reference for major membrane protein at ~39 kDa (OMP).

Within desorption conditions at 300 mM NaCl, only 15% respectively 17% of non-target proteins in comparison with crude and cleared homogenate were detected after extraction. At same conditions 6% and 12% of protein from light homogenate fraction were respectively found in supernatant Further, homogenate supernatant and eluted protein were compared after incubation of cells with 70% v/v ground AMBERLITE® IRC 748 and ground MARATHON® A2 at pH 8.0 in 50 mM TRIS for 2 hours at mixing at static conditions, respectively. Aliquots of suspension were diluted 1:2 in 50 mM TRIS buffer or 1 M NaCl. SD S-Page of all samples was performed at the same dilution ration and densitometry of Coomassie staining was used for appreciation of protein amounts.

Figure 13:
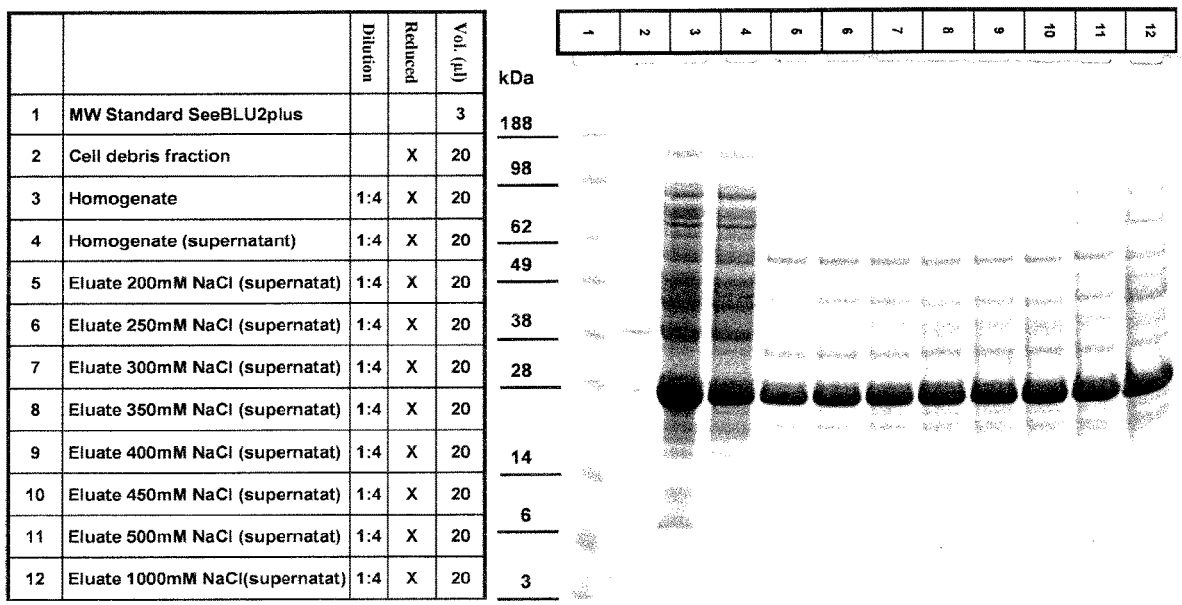
FIG. 13: Extraction of non-target proteins by 3 hour incubation (50 mM TRIS, pH 8.0) of GFP expressing E. coli with MARATHON® A2 microparticles (50% volumetric resin:cells ratio) after elution with different NaCl concentrations (200-1000 mM) in comparison to E. coli homogenate and homogenate supernatant determined by SDS-Page and Coomassie staining.
Figure 14:
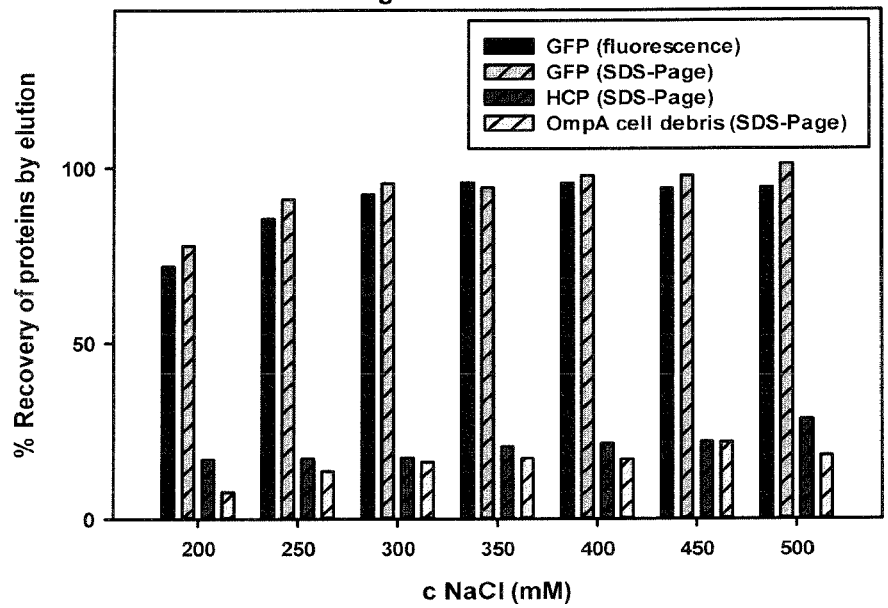
FIG. 14: Densitometry analysis of the SDS-Page from FIG. 13.
Figure 15:
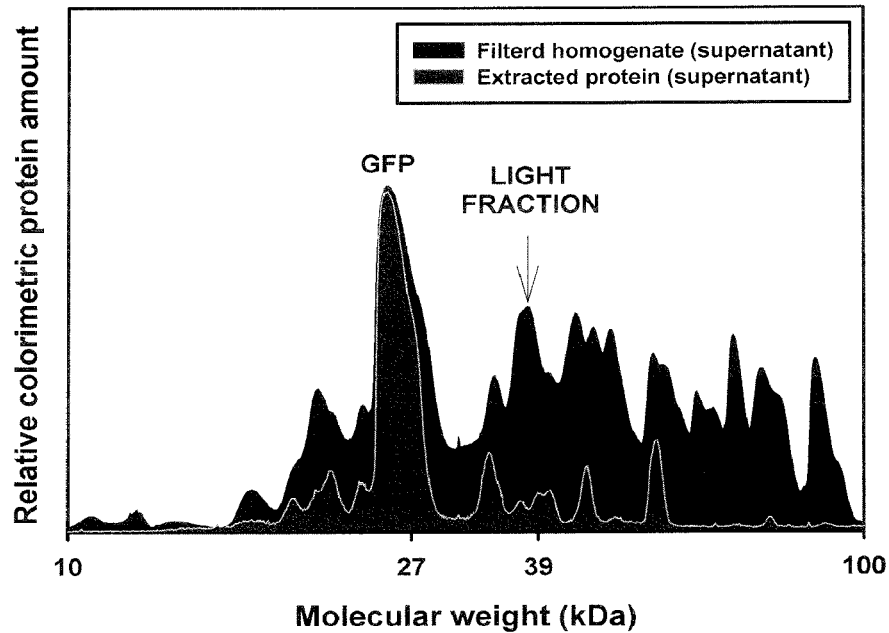
FIG. 15: Protein profile of GFP expressing E. coli homogenate supernatant in comparison to eluate obtained from E. coli by 3 hour static incubation (50 mM TRIS, pH 8.0) with MARATHON® A2 microparticles (50% volumetric resin:cells ratio) and elution with 300 mM NaCl.
Figure 16C:
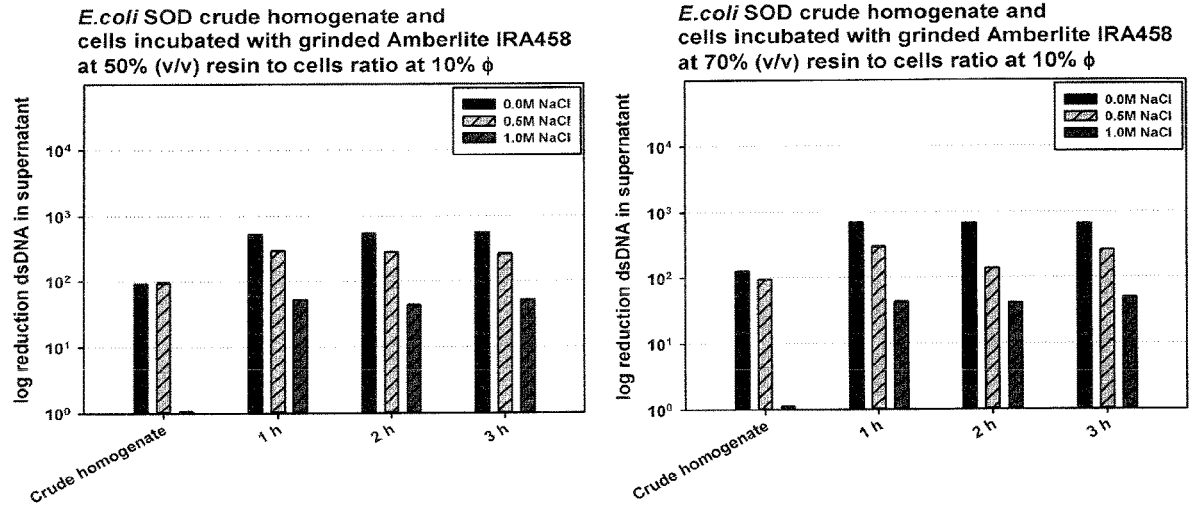
FIG. 16C shows the dsDNA reduction kinetics during extraction of protein (SOD) using 1000% v/v resin:cells of AMBERLITE® IRA458.
Figure 16C:
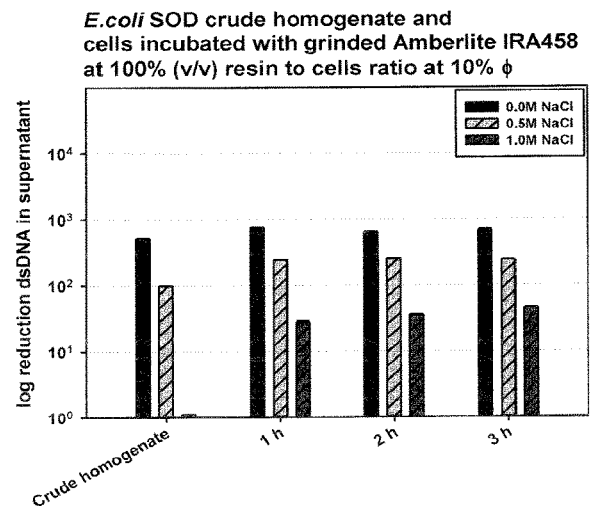

GFP recovery was evaluated by densitometry of SDS-Page (Coomassie) and compared to eluted host cell proteins, in particular membrane proteins (FIGS. 13, 14, 15). Extracted proteins were compared after incubation of cells with 50% v/v ground MARATHON® A2 at pH8.0 for 3 h in 50 mM TRIS. Aliquots of suspension were eluted by 1:2 dilutions in 200, 250, 300, 350, 400, 450, 500 and 1000 mM NaCl. SDS-Page of all samples was performed at same dilution ratio and densitometry of Coomassie staining was used for appreciation of protein amounts (FIG. 13). GFP was recovered to almost 100% in supernatant at 300 mM NaCl from MARATHON® A2. Desorption at higher salt concentrations caused recovery of higher amounts of non-target and light fraction proteins (FIG. 14). On average 15% light fraction protein and 20% of non-target proteins were extracted respectively from cells with microparticles in comparison with high pressure homogenization in supernatant.

The profile of detected proteins by Coomassie staining showed purity differences between the supernatant of cells disrupted by HPH and by extraction with microparticles. The protein profile of homogenate supernatant and eluted protein with 300 mM NaCl after incubation of cells with 50% v/v ground MARATHON® A2 at pH8.0 in 50 mM TRIS for 3 his shown in FIG. 15. SDS-Page of samples was performed at same dilution ratio and densitometry of Coomassie staining was used for appreciation of relative protein amounts. Relative purity for GFP was 9.8% in homogenate and 37.4% in elute at 300 mM NaCl and on average at 33.2%±2.9% after extraction.

In another approach, the protein profile of homogenate supernatant and extracted protein was determined after incubation of cells with 70% ground AMBERLITE® 748 at pH 8.0 in 50 mM TRIS for 2 hours. SDS-Page of samples was performed at the same dilution ration and densitometry of Coomassie staining was used for appreciation of relative protein amounts. Relative purity of GFP was 12.4% in homogenate and 38.4% in supernatant and on average at 41.6%±2.7% after extraction.

The non-target protein reduction during extraction kinetic of protein (SOD) from cell suspension ($E.$ $coli$) with cationic resin (MARATHON® A2) after static incubation in 50 mM TRIS buffer at pH 8.0 (10% v/v) and subsequent elution with NaCl was determined. Non-target proteins amount was estimated by densitometry from SDS-Page. The purity of SOD extracted from cells was two times higher than of that captured from homogenate by styrenic micro particles.

Example 6: SOD Activity

Enzymatic activity of SOD extracted from cells by styrenic cationic microparticles MARATHON® A2 (MA2) was determined after extraction from cell suspension ($E.$ $coli$) and homogenate after static incubation in 50 mM TRIS buffer at pH 8.0 at 70% v/v volume ration of resin:cells (10% v/v) and subsequent elution with 0.5 M NaCl. Supernatants were centrifuged (1 ml, 30 min, 23° C. and 16000 rcf), filtered (PVDF membrane, 0.2 µm) and diluted in 1:10 steps with respective buffer to an effective measurement range. SOD activity was determined by 19160 SOD determination kit purchased from Sigma. Enzymatic activity of SOD extracted from cells by MA2 microparticles was on average increased by one unit compared to that captured from homogenate.

Example 7: Contaminants

DNA was quantified with Quant-iT™ PicoGreen® dsDNA Assay Kit purchased from Invitrogen. Endotoxin was quantified with PyroGene™ Recombinant Factor C Assay purchased from Lonza. All supernatant samples were centrifuged (1 ml, 30 min, 23° C. and 16000 rcf), filtered (PVDF membrane, 0.2 µm) and diluted in 1:10 steps with respective buffer to an effective measurement range Measurements were performed accordingly to respective kit instruction notes on plate reader (GENios Pro or Infinite 200M from Tecan).

Example 7.1 dsDNA

The reduction of dsDNA was determined during the extraction of protein (SOD) from a cell suspension ($E.$ $coli$) with acrylic (AMBERLITE® IRA458) and cationic resin (MARATHON® A2) after static incubation in 50 mM TRIS buffer at pH8.0 at 50, 70, 100% v/v volume ratio of resin to cells (10% v/v) and subsequent elution with NaCl. DNA was quantified as described above. Up to $10^2$ less dsDNA was released by incubation of cells with microparticles. At protein elution conditions (0.5 M NaCl), dsDNA reduction in the supernatant was between $10^2$ and $10^3$ (FIGS. 16A-16F).

Example 7.2 Endotoxin

Endotoxin reduction was determined during extraction kinetic of protein (SOD) from cell suspension ($E.$ $coli$) with cationic resin (MARATHON® A2). after static incubation in 50 mM TRIS buffer at pH 8.0 (10% v/v) and subsequent elution with NaCl. Endotoxin amount was quantified as described above.

Figure 17:
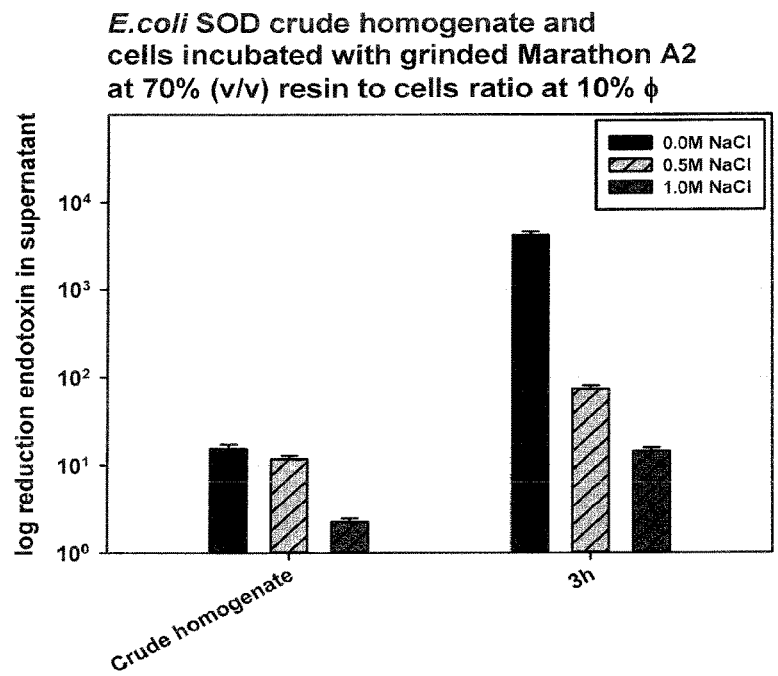
FIG. 17: Endotoxin reduction during extraction kinetic of protein (SOD) from E. coli homogenate and cell suspension (10% v/v) with MARATHON® A2 microparticles after static incubation (50 mM TRIS, pH8.0) and subsequent elution with NaCl. Endotoxin amount was estimated by PyroGene™ Recombinant Factor C Assay purchased from Lonza.

At extraction conditions $10^3$ less endotoxin was released to the supernatant in comparison to adsorption from the homogenate (FIG. 17). At 0.5 M NaCl and 1.0 M NaCl endotoxin was about 10× reduced.

Example 8: Microscopy

Example 8.1 Atomic Force Microscopy (AFM)

Positively charged microscopic slides were sequentially treated with sucrose (50 mM) solution, deionised water and diluted suspension of microparticles. After each step drying was performed at 65° C. for 24 h. Measurements were carried out at the Department of Nanobiotechnology, BOKU (Dr. Gerhard Sekhot).

Figure 18:
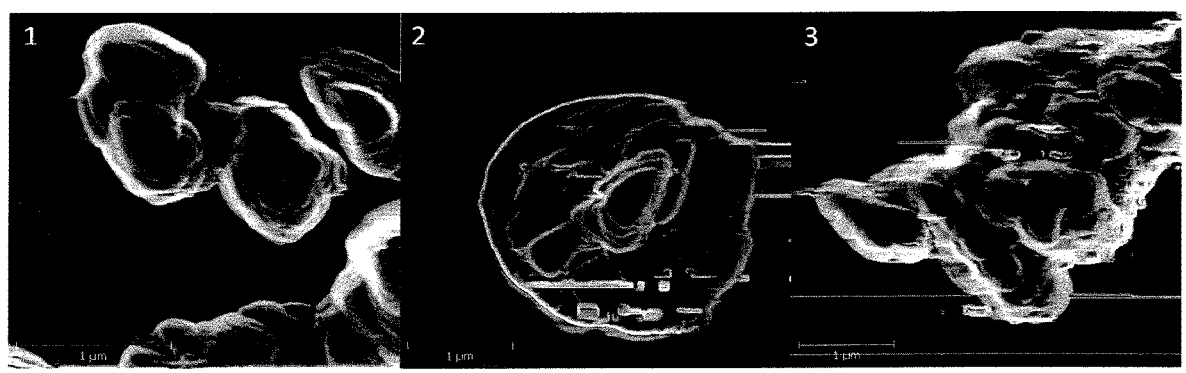
FIG. 18: Atomic force microscopy (AFM) of ground resins. Height measurement of MARATHON® A2 (Image 1), MARATHON® MSC (Image 2) and AMBERLITE® IRC748 (Image 3).

The open source software Gwyddion (v2.60) was used for visualisation of AFM data. An edged surface topography was apparently generated as a consequence of mechanical abrasion of original beads. Ground particles had similar surface topography (FIG. 18).

Figure 19:
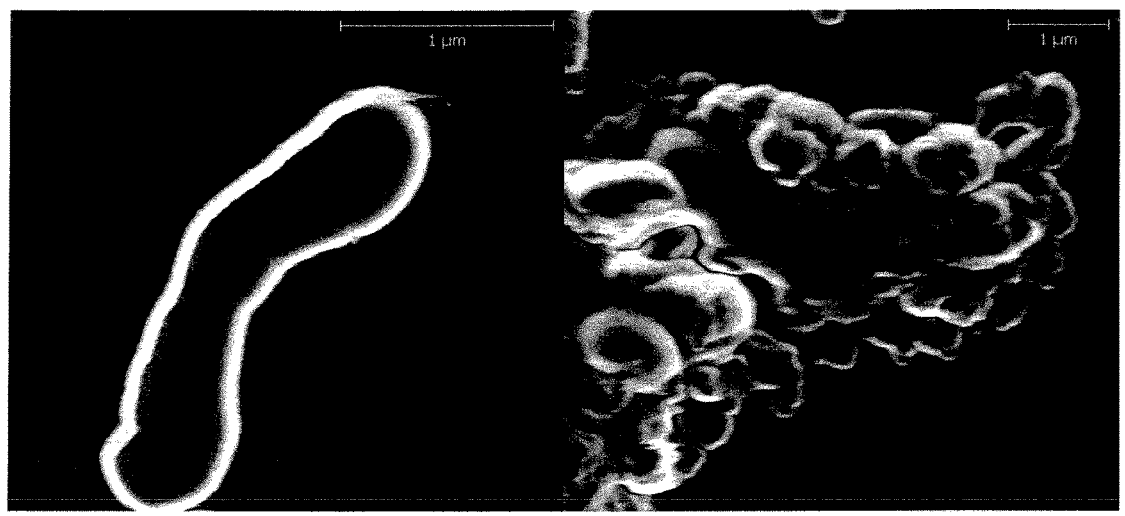
FIG. 19: Atomic force microscopy (AFM) of *E. coli* cells. Height measurement of cells before (left side) and after 1 h incubation with ground MARATHON® A2.

Images generated by AFM (FIG. 19) of E. coli before and after incubation with ground MARATHON® A2 indicated that protein was extracted without fragmentation of cells.

Example 8.2 Optical Microscopy

Confocal and fluorescence microscopy were performed at Vienna Institute of Biotechnology (VIBT) on Leica "Live Cell" wide-field microscope. Samples were diluted to ~1% v/v solids concentration in respective buffer and visualized at 1000× magnification (Leica HCX PL APO 100×1.4 oil).

Figure 20:
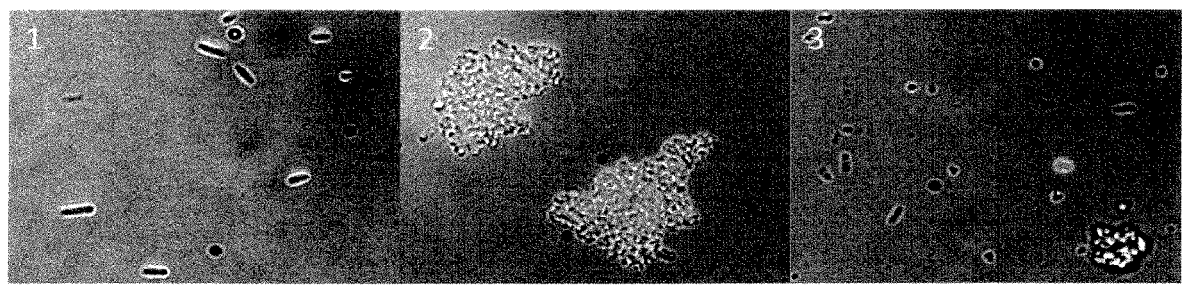
FIG. 20: Overlaid images of *E. coli* HMS174 (GFP-mut3.1) without microparticles (picture 1), after 1 h incubation with ground MARATHON® A2 (picture 2) and with ground AMBERLITE® IRC748 (picture 3) at pH8.0 in 50 mM TRIS.

Bright field (BF), differential interference contrasts (DIC) and fluorescence microscopy was performed at 1000× magnification. Cells were mobile and bright fluorescent at default excitation and emission wavelengths of GFP. Cells were immobilized by adsorption on microparticles (FIG. 20).

Example 9: Cell Viability

Example 9.1 BacLite

Figure 21:
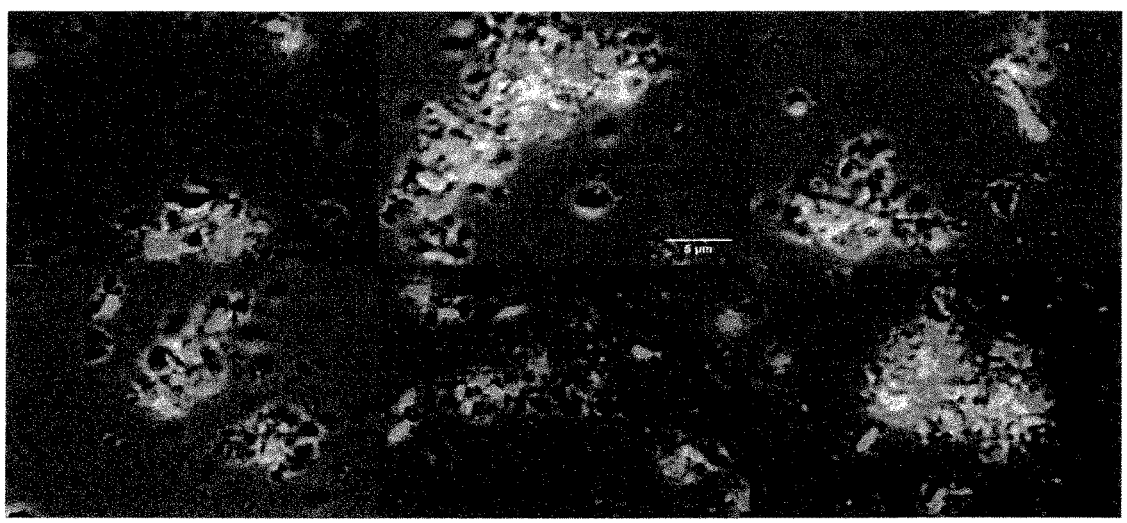
FIG. 21: Viability of *E. coli* cells (10% v/v) after 2 hours of static incubation (50 mM TRIS, pH8.0) with MARATHON® A2 microparticles (70% volumetric resin:cells ratio) and 1:10 dilution in physiological buffer. Live (green)/dead (red) cell staining was performed with "BacLite" fluorometric staining kit from Invitrogen.

Viability of E. coli cells (10% v/v) after 2 hours of static incubation (50 mM TRIS, pH 8.0) with MARATHON® A2 microparticles (70% volumetric resin:cells ratio) and 1:10 dilution in physiological buffer. Cells were stained with "BacLite" (Invitrogen). Live (green) and dead (red) cells are shown in FIG. 21.

Example 9.2 Koch's Plates

Cell viability was determined after 3 h of static incubation of E. coli cells (10% v/v) with microparticles obtained from ground MARATHON® A2 and AMBERLITE® IRA 458 (70% v/v resin:cells ratio) in 50 mM TRIS and pH 8.0. Cells (E. coli GFP) and cells/resin suspensions (1 ml aliquots) were diluted progressively and mixed vigorously 1:10 in sterile 0.9% w/w NaCl. Nutrient agar (NA) for microbiology Merck 20 g/l in ddH$_2$O was heated in a steam autoclave at 121° C. for 15 min. Aliquots (1 ml) of diluted suspensions were poured into culture dishes and mixed with 55° C. tempered NA solution. Gel formation was considered completed after 30 min at room temperature and plates were incubated overhead at 37° C. for 30 h.

Up to $10^3$ more colony forming units (CFU) were determined after incubation with cationic microparticles. Relevant CFU values for microparticles were obtained after 1000 dilution in physiological buffer which indicated that adsorbed cells could not propagate.

Identity of cells was determined by optical microscopy from 10× dilutions of cells without resin and cells at 1000× dilutions after GFP extraction with cationic microparticles. Size, shape and fluorescence correspond to E. coli GFP.

Example 10: Hydrophobic Microparticles

Preparation of Hydrophobic Microparticles

Adsorbent type resin provided by DOW: AMBERLITE® XAD4, AMBERLITE® XAD7HP and AMBERLITE® XAD761 were purchased from Sigma Aldrich, Vienna, Austria, 2011.

Resins were grinded overnight (20 g for ~12 h) with an electric motor driven, ceramic coated mortar. Grinded resins were suspended in water (~10% v/v and ad. 50 ml). Supernatant was centrifuged for 30 min at 4000×g (equivalent with relative centrifugal force). Resins were re-suspended in 2 M sodium chloride (50 ml) centrifuged for 1 min (4000×g). Pellet of 1 min centrifugation was discarded. Supernatant were transferred and centrifuged again for 30 min (4000×g). Supernatant was discarded. Grinded resins were re-suspended (1:2) in water and transferred to tubes. Resins were centrifuged at 4000×g, supernatant was discarded and resin was re-suspended in 50 ml of aqueous washing solution.

Wash sequence was:
1×50% EtOH (dilution of organic residues)
3× deionized water (dilution of EtOH)

Particle Size of Hydrophobic Microparticles

Particle size distributions of microparticles were calculated from equivalent circular diameter by measurement of bright field microscopy projections of approximately 500 particles at 1% v/v and 600× fold magnification.

General Protocol for Microparticles and Conventional Chromatographic Media Adsorption/Desorption Adsorption and desorption studies were performed in 1 mL batches (homogenate or standard protein solution). Various amounts of 50% (v/v) microparticles suspensions (in μL), were added to protein solutions in 2 mL tubes. Dilution factor concerning protein concentration and conductivity was taken into account.

Microparticles suspensions were incubated for 30 minutes, conventional chromatographic media suspension for 12 hours. Afterwards microparticles or conventional chromatographic media were centrifuged at 7000×g for 10 min and elution of bound protein was performed by addition of 1 mL elution buffer, vigorous mixing and incubation for 30 min. In some cases a second washing step with elution buffer was included. After elution microparticles or conventional chromatographic media were centrifuged again as before. Concentration of protein in supernatants was quantified by photometric analysis and purity of target protein was checked by SDS-PAGE.

Example 11: Recovery of Acidic Biomolecules

Batch adsorption of recombinant GFP from E. coli crude homogenate was performed using Microparticles (MPs) (ground chromatography resin MARATHON® A2 (MA2)) with the following steps. This Example uses GFP as acidic intracellular soluble protein.

E. coli strain HMS174(DE3)(pET11aGFPmut3.1) was fermented in a 5 L scale fed-batch process. The expression of the intracellular soluble target protein GFP (green fluorescent protein) was induced using IPTG (Isopropyl β-D-1-thiogalactopyranoside).

Harvest and Homogenization: The E. coli suspension (biomass content ~30% wt) was cooled to 4° C. and centrifuged at 15000 g for 20 min. The supernatant was discarded and the cell pellet was further processed. The cell pellet was resuspended in 50 mM Tris, pH 7.5 and diluted to a biomass content 20% wt cells/buffer. Cells were disrupted by high pressure homogenization at 1000 bar for two passages producing the crude cell lysate.

For the batch adsorption from *E. coli* lysate it is also possible to use frozen biomass. In this case the biomass (20% w/v) is resuspended in 50 mM Tris, pH 7.5, and same disruption procedures can also be applied as is the case for fresh fermented *E. coli* cells.

Capture of the Target Protein

The batch adsorption was performed in tubes in small scale of 1 mL volume as well as in scales up to 100 mL in glass beakers at room temperature (rt). To the crude cell lysate MA2 was added (1 µL of 50% v/v % MA2 were added per 1 µg cell pellet) and mixed for ~5 s in a lab vortex or in bigger scale with an overhead stirrer for ~30 s. During mixing the flocculation took place and the MA2 bound to the target protein as well as impurities like DNA, hcps (host cell proteins) and cell fragments. After the flocculation the samples were centrifuged for 3 min at 13400 g or filtrated using a 0.2 µm filter plate at 1.5 bar in a dead-end filtration with overhead pressure. The supernatant was discarded and the pellet/filter cake further processed for the wash step.

Flocculate Wash

The pellet of the flocculate was resuspended in a 50 mM Tris wash buffer with 75 mM NaCl at pH 7.5. After short incubation the flocculate was separated using centrifugation (13400 g for 3 min). When the separation took place using a filtration process the filter cake was not resuspended but washed by filtrating the wash buffer through the filter cake (0.2 µm filter plate at 1.5 bar). The supernatant was discarded and the pellet/filter cake further processed for the elution step. The low salt concentration is able to elute impurities with low binding strength.

Elution: For the elution step the washed flocculate was resuspended in 50 mM Tris buffer containing 400 mM NaCl at pH 7.5. The flocculate was mixed in a tumbler for 5 min. At 400 mM NaCl concentration the target protein elutes from the MPs and is now in the supernatant. The supernatant was separated from the flocculate using centrifugation (13400 g for 3 min) or per dead-end filtration (0.2 µm filter plate at 1.5 bar). The pellet/filter cake containing the MPs with bound impurities was discarded and the supernatant containing the protein of interest (GFP) was processed further.

Figure 22:
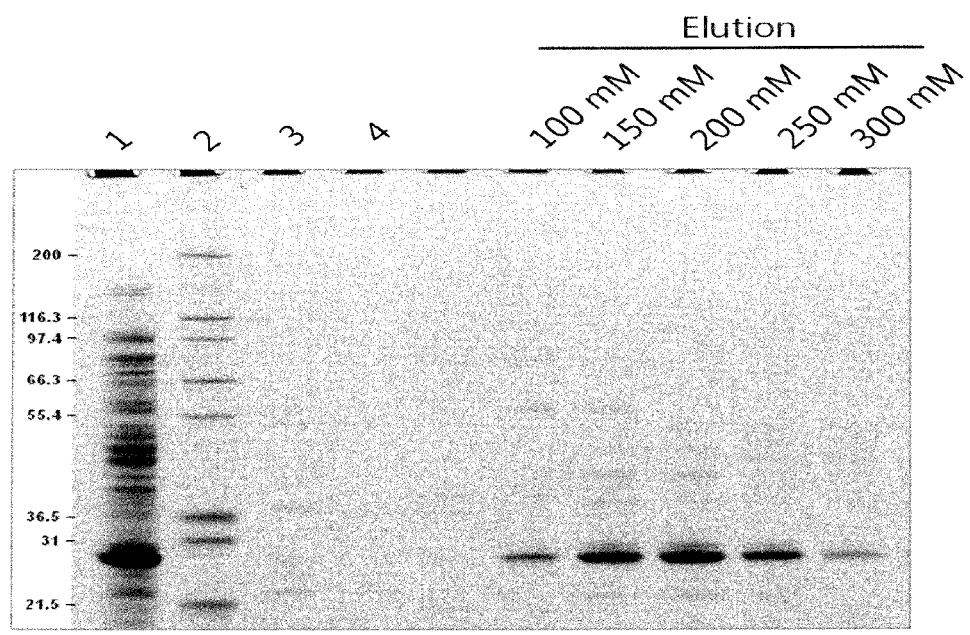
FIG. 22: SDS-Gel shows an elution profile using microparticles to capture GFP from cell homogenate.

Elution profile of the GFP is shown in FIG. 22. The lysate sample can be seen on lane 1 which is the starting material for the purification process. Lane 2 is the marker (Mark12™). Lane 3 shows the supernatant after capture. The missing GFP band shows that all GFP molecules are bound to the MPs. On lane 4 is the wash step. The elution takes place between 100-400 mM NaCl. Pooling of the elution samples provided a yield of 98% and lane purity about 60% for GFP.

Example 12: Recovery of Basic Biomolecules Using Positively Charged Microparticles This example demonstrates the recovery of recombinant expressed basic proteins using MPs from ground MARATHON® A2 (MA2) resin from cell homogenate. The protein Interferon Gamma, IFN-γ, functions as an example for an intracellular soluble expressed basic protein. This example shows that the positively charged exchange resin can be used for biomolecule recovery by binding to unwanted cellular structures and intracellular material (referred to as negative purification).

IFN-γ was expressed intracellularly soluble in *E. coli* by fed-batch fermentation.

Harvest and Homogenization

Frozen biomass (20% w/v) of cells which express Interferon Gamma IFN-γ was used and resuspended in lysis buffer (20 mM Tris, 10 mM EDTA, 1 M Urea, 0.1% beta-mercaptoethanol). The cells were disrupted by high pressure homogenization at 950 bar for three passages producing the crude cell lysate. The cell disruption would also work with fresh biomass.

Negative Purification of the Target Protein

The batch adsorption was performed in tubes in small scale of 2 mL volume at room temperature (rt). The crude cell lysate was mixed with MA2 (50% v/v) and mixed for ~5 s in a lab vortex (0.7 µL of 50% v/v MA2 added per 1 µg wet cell pellet). During mixing the flocculation takes place where MA2 binds negatively charged impurities like DNA, hcps (host cell proteins) and cell fragments. After the flocculation the samples were centrifuged for 3 min at 13400 g or filtrated using a 0.2 µm filter plate at 1.5 bar in a dead-end filtration with overhead pressure. The pellet/filter cake containing the MPs with bound impurities was discarded and the supernatant containing the protein of interest (IFN-γ) was processed further.

Figure 23:
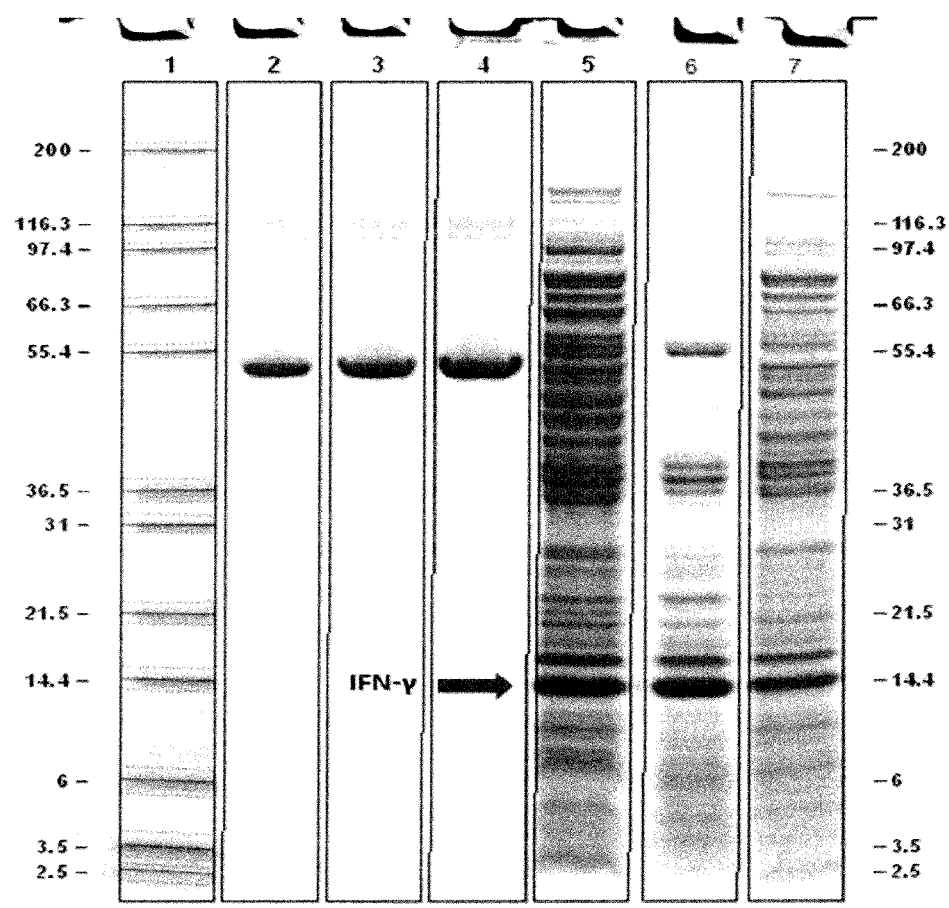
FIG. 23: SDS-Gel shows an elution profile using microparticles to for recovering IFN-γ from cell homogenate.

Elution profile of the Interferon Gamma IFN-γ is shown in FIG. 23. On lane 1 is the marker Mark12' followed by BSA on lanes 2-4 for quantification purposes. On lane 5 is the cell homogenate. On lane 6 is the supernatant sample the addition of positively charged microparticles (MARATHON® A2) that bind HCPs DNA and cell fragments. Lane 7 shows an exemplary pellet wash & strip with 1000 mM NaCl to elute the impurities. The yield is up to 99% with a purity of 30%.

Example 13: Recovery of Acidic Biomolecules Using Positively Charged Microparticles from *E. coli* Cells This example shows the extraction of an acidic intracellular soluble protein from intact *E. coli* cells using positively charged MPs prepared from MA2. In this example the used target protein is GFP. The protein extraction was shown using two different *E. coli* strains, HMS174(DE3) and BL21 each with a different GFP molecule GFPmut3.1 and GFP.1 respectively. Two variants for the protein extraction were carried out Example 13.1

*E. coli* strains HMS174(DE3)(pET11aGFPmut3.1) and BL21(pB11KT7ix.1_GFP.1) were fermented in a 5 L scale fed-batch process. The expression of the intracellular soluble target protein GFP (green fluorescent protein) was induced using IPTG (Isopropyl β-D-1-thiogalactopyranoside).

Cell Harvest & Wash

The cells were harvested and stored overnight (~12 h) at 4° C. in FLEXBOY® Bags. The *E. coli* suspension (biomass content ~30% wt) was cooled to 4° C. and centrifuged at 15000 g for 20 min and later resuspended with a 50 mM Tris buffer at pH 7.5 while containing the same biomass content.

Cell Flocculation and Protein Recovery

Example 13.1 uses reduced amount of MPs (85 µL MA2 (50% v/v) per 1 mL cell suspension at 30% wet biomass content) to bind and flocculate the *E. coli* cells. While the MPs were in contact with the cells, the extraction took place and the target protein (here GFP) were be released and accumulated in the supernatant. After an incubation of 2-3 h the extraction was complete and the flocculated cells were separated using dead-end filtration (0.2 μm filter plate at 1.5 bar) or centrifugation (13000 g for 3 min). The cell pellet/filter cake was discarded and the supernatant containing the target protein was further processed.

Example 13.2

In this Example more microparticles were added to the cell suspension. The higher amount of microparticles allowed the binding and extraction of the target protein directly.

E. coli strains HMS174(DE3)(pET11aGFPmut3.1) and BL21 (pB11KT7ix. 1_GFP.1) were fermented in a 5 L scale fed-batch process. The expression of the intracellular soluble target protein GFP (green fluorescent protein) was induced using IPTG (Isopropyl β-D-1-thiogalactopyranoside).

Cell Harvest & Wash

The cells were harvested and stored overnight (~12 h) at 4° C. in FLEXBOY® Bags. The E. coli suspension (biomass content ~30% wet) was cooled to 4° C. and centrifuged at 15000 g for 20 min and later resuspended with a 50 mM Tris buffer at pH 7.5 while containing the same biomass content.

Cell Flocculation and Protein Recovery

Example 13.2 uses a higher amount of microparticles (350 μL MA2 (50% v/v) per 1 mL cell suspension at 30% wet biomass content) compared to Example 13.1 to bind and flocculate the E. coli cells. While the microparticles were in contact with the cells, the extraction of the target protein took place and the proteins were directly bound by the MPs. After incubation between 1.5 to 2.5 h the extraction was completed. The supernatant was separated using dead-end filtration (0.2 μm filter plate at 1.5 bar) or centrifugation (13000 g for 3 min). The supernatant was discarded and the pellet of the flocculate the target protein was further processed.

Flocculate Wash

The pellet of the flocculate was resuspended in a 50 mM Tris wash buffer with 75 mM NaCl at pH 7.5. After short incubation the flocculate was separated using centrifugation (13400 g for 3 min). When the separation took place using a filtration process, the filter cake was not resuspended but washed by filtrating the wash buffer through the filter cake (0.2 μm filter plate at 1.5 bar). The supernatant was discarded and the pellet/filter cake further processed for the elution step. The low salt concentration is able to elute impurities with low binding strength.

Elution

For the elution step the washed flocculate is resuspended in 50 mM Tris buffer containing 400 mM NaCl at pH 7.5. The flocculate was mixed in a tumbler for 5 min. At 400 mM NaCl concentration the target protein elutes from the MPs and is now in the supernatant. The supernatant was separated from the flocculate using centrifugation (13400 g for 3 min) or per dead-end filtration (0.2 μm filter plate at 1.5 bar). The pellet/filter cake containing the MPs with bound impurities was discarded and the supernatant containing the protein of interest (GFP) was processed further.

Figure 24:
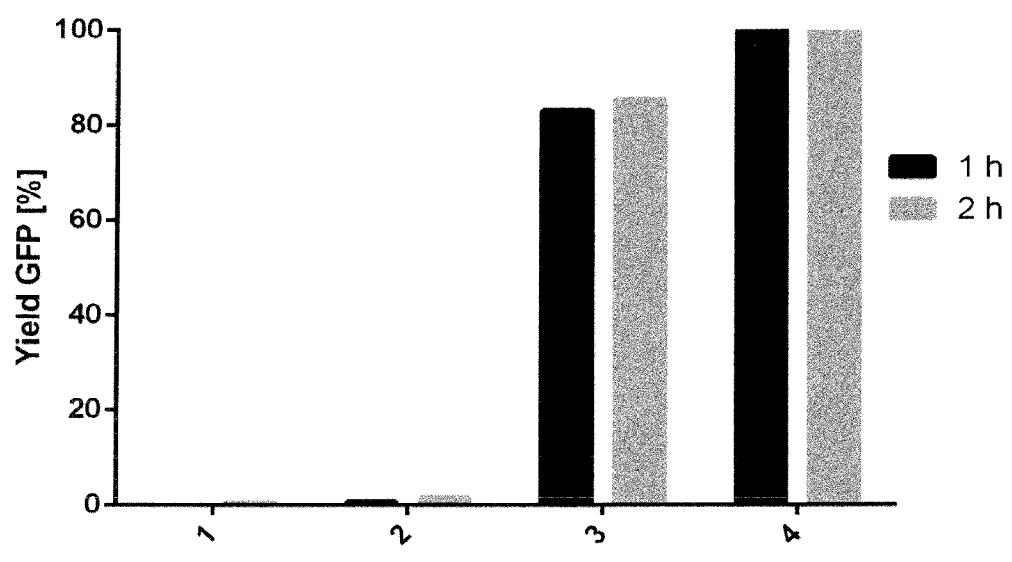
FIG. 24: Bar graph showing the GFP amount in the capture supernatant (1) and wash buffer (2), eluted GFP (3) in Example 13.2 compared with maximum GFP using chemical disruption method (4).

FIG. 24 is a bar graph showing the GFP yield from Example 13.2 for two different incubation times: 1 h and 2 h. 1 shows the GFP amount in the capture supernatant. 2 shows the GFP amount in the wash buffer in the washing step of the flocculate. No GFP leakage can be seen in 1 or 2. 3 shows the elution with 400 mM NaCl in 50 mM Tris, where the GFP was eluted from the MPs and accumulated in the supernatant. 4 shows the maximum amount of GFP in the cells which were lysed using a chemical disruption method.

Example 14: Recovery of a Basic Protein from Cells Using Positively Charged Microparticles Positively charged microparticles are prepared from grinding DOWEX® M-A2 anion exchange resins to obtain microparticles as described in Example 1.

IFN-γ was expressed inracellularly soluble in E. coli by fed-batch fermentation.

Cell Harvest & Wash

The cells were harvested and stored overnight (~12 h) at 4° C. in FLEXBOY® Bags. The E. coli suspension (biomass content ~30% wt) was cooled to 4° C. and centrifuged at 15000 g for 20 min and later resuspended with a buffer (20 mM Tris, 10 mM EDTA, 1 M Urea, 0.1% beta-mercaptoethanol) while containing the same biomass content.

Cell Flocculation and Protein Recovery

MPs (85 μL MA2 (50% v/v) per 1 mL cell suspension (at 30% wet biomass content) are added to the cell suspension to bind and flocculate the E. coli cells. While the MPs were in contact with the cells, the extraction took place and the target protein (here IFN-γ) was released and accumulated in the supernatant. After an incubation of 2-3 h the extraction was complete and the flocculated cells were separated using dead-end filtration (0.2 μm filter plate at 1.5 bar) or centrifugation (13000 g for 3 min). The cell pellet/filter cake was discarded and the supernatant containing the target protein was further processed.

Example 15: Recovery of Basic Proteins from Cells Using Negatively Charged, Chelating Microparticles Microparticles are prepared from chelating cation exchange resin AMBERLITE® IRC748.

IFN-γ was expressed inracellularly soluble in E. coli by fed-batch fermentation.

Cell Harvest & Wash

The cells were harvested and stored overnight (~12 h) at 4° C. in FLEXBOY® Bags. The E. coli suspension (biomass content ~30% wt) was cooled to 4° C. and centrifuged at 15000 g for 20 min and later resuspended with a buffer (20 mM Tris, 10 mM EDTA, 1 M Urea, 0.1% beta-mercaptoethanol) while containing the same biomass content.

Cell Flocculation and Protein Recovery

MPs (85 μL AMBERLITE® IRC748 (50% v/v) per 1 mL cell suspension (at 30% wet biomass content) are added to the cell suspension to bind and flocculate the E. coli cells. While the MPs were in contact with the cells, the extraction took place and the target protein (here IFN-γ) was released and accumulated in the supernatant. After an incubation of 2-3 h the extraction was complete and the flocculated cells were separated using dead-end filtration (0.2 μm filter plate at 1.5 bar) or centrifugation (13000 g for 3 min). The cell pellet/filter cake was discarded and the supernatant containing the target protein was further processed.

Example 16: Preparation of Microparticles from Ion Exchange Resins

Different types of ion exchange resins were purchased from Sigma Aldrich and DIAION®.

The following anion exchanger resins were used: AMBERLITE® IRA-400, AMBERLITE® IRA-743, DOWEX® 1×2-100, DOWEX® 1×2-400, DOWEX® 1×8-100, MARATHON® A2, DIAION® SA20A, DIAION® SA10A, DIAION® SA312.

The following cation exchanger resins were used: DOWEX® 50 WX2-100, DOWEX® 50 WX8-100, MARATHON® C, MARATHON® MSC, DIAION® PK216, DIAION® SK110.

Resins were wet ground (20 g for ½ h) in a coated ceramic mortar by hand for ca. 30 min. Ground resins were suspended in water (ad 50 ml). After a period (ca. 96 h) supernatant of resins sediment was transferred to tubes. Supernatant was piecewise (1 ml) centrifuged for 15 min at 7000 rcf (relative centrifugal force) until ca. 200 μl resin was collected per tube. Resins were re-suspended in 2M Sodium chloride (1.5 ml) an centrifuged for 1 min (7000 rcf). Pellet of 1 min centrifugation was discarded (excepting AIVIBERLITE® IRA-743). Supernatant were transferred and centrifuged again for 15 min (7000 rcf). Supernatant of 15 min centrifugation was discarded. Micro particles (ca. 200 μl) were also centrifuged in 2M Sodium chloride. Micro particles (ca. 150 μl) and other ground resins (50-200 μl) were re-suspended (1:4) in water and transferred in portions (50 μl resin) to tubes.

Aliquots of resin were centrifuged at 7000 rcf, supernatant was discarded and resin was re-suspended in 20 fold volume (about 1 ml) of aqueous washing solution. Time of incubation in solution was 30 min.

Wash Sequence:
1×50% EtOH (dilution of organic residues)
3× deionized water (dilution of EtOH)
Check for near neutral pH
re-suspension of micro particles and ground resin in deionized water (about 70% v/v)
Resins were equilibrated in corresponding buffer used for specific experiments.

Determination of Particle Size Using Optical Microscopy

Particle size of the prepared microparticles was determined by optical microscopy using a software-based determination of size. Particle size of ground materials and micro particles was measured at 1000 fold magnification by estimation of relative diameter. Distribution was calculated by comparison of diameter sizes of 1000-5000 particles at 1% v/v. Results are shown in Table 3.

|  | Ligand | d (mm) | q BSA |
|---|---|---|---|
| Type anion exchanger | | | |
| AMBERLITE ® IRA-400 | —N$^+$—(CH$_3$)$_3$ (Type 1) | 0.3-1.2 | 0.3 ± 0.11 |
| AMBERLITE ® IRA-743 | Methylglucamine | 0.5-0.7 | 6.1 ± 0.25 |
| DOWEX ® 1X2-100 | —N$^+$—(CH$_3$)$_3$ (Type 1) | 0.1-0.5 | 0.5 ± 0.18 |
| DOWEX ® 1X2-400 | —N$^+$—(CH$_3$)$_3$ (Type 1) | 0.04-0.07 | 0.8 ± 0.01 |
| DOWEX ® 1X8-100 | —N$^+$—(CH$_3$)$_3$ (Type 1) | 0.1-0.5 | 0.4 ± 0.03 |
| MARATHON ® A2 | —N$^+$—(CH$_2$—CH$_2$OH)—(CH$_3$)$_2$ (Type 2) | 0.4-0.6 | 0.2 ± 0.02 |
| DIAION ® SA20A | Dimethylethanolamine | 0.3-1.18 | n.a. |
| DIAION ® SA10A | Trimethylamine | 0.3-1.18 | n.a. |
| DIAION ® SA312 | Trimethylamine | 0.3-1.18 | n.a. |
| Type cation exchanger | | | |
| DOWEX ® 50 WX2-100 | —SO$_3^-$ | n.a. | n.a. |
| DOWEX ® 50 WX8-100 | —SO$_3^-$ | n.a. | n.a. |
| MARATHON ® C | —SO$_3^-$ | 1.2 | n.a. |
| MARATHON ® MSC | —SO$_3^-$ | 1.2 | n.a. |
| DIAION ® PK216 | Sulphonic | 0.3-1.18 | n.a. |
| DIAION ® SK110 | Sulphonic | 0.3-1.18 | n.a. |

Table 3 lists resins used for preparation of microparticles.

What is claimed is:

1. A method of manufacturing a protein of interest comprising:
    (a) cultivating a host cell that produces the protein of interest in a biological fluid; and
    (b) recovering the protein of interest from the biological fluid by:
        (i) adding to the biological fluid positively-charged microparticles comprising a ground polymeric anion exchange resin or negatively-charged microparticles comprising a ground polymeric cation exchange resin, and
        (ii) recovering the proteins of interest from the biological fluid;
    wherein a mixing of the microparticles with the biological fluid causes a disruption of the cells or extraction of the proteins of interest from the cells.

2. The method of claim 1, wherein the method further comprises:
    (c) purifying the protein of interest.

3. The method of claim 2, wherein the method further comprises modifying the protein of interest, preparing a pharmaceutical formulation comprising the protein of interest, or both.

4. The method of claim 1, wherein the protein of interest is a recombinant protein.

5. The method of claim 1, wherein the host cell expresses the protein of interest.

6. The method of claim 1, wherein the biological fluid is a cell culture, cell suspension, fermentation broth, culture broth, fermentation supernatant, culture supernatant, or cell supernatant.

7. The method of claim 1, wherein the microparticles form flocculus.

8. The method of claim 1, wherein the anion-exchange resin and the cation exchange resin are polystyrene-based, Hydroxyethyl methacrylate (HEMA)-based, dimethylamino ethylmethacrylate (DMAEMA)-based, dimethylamino ethylmethacrylate (pDMAEMA), polyacrylamide based, or methacrylic acid (MAA)-based.

9. The method of claim 1, wherein the cation exchange resin and anion-exchange resin are polystyrene cross-linked with divinylbenzene.

10. The method of claim 1, wherein the microparticles have an average particle size of less than about 5 μm.

11. The method of claim 1, wherein the positively-charged microparticles or negatively-charged microparticles are produced by grinding a polymeric anion-exchange or cation-exchange resin, respectively.

12. The method of claim 1, wherein the cells are eukaryotic or prokaryotic cells.

13. The method of claim 1, further comprising allowing the microparticles to form a flocculus before recovering the proteins of interest from the biological fluids.

14. The method of claim 13, wherein recovering the proteins of interest from the biological fluids in step (b)(ii) comprises removing the flocculus from the biological fluids and desorbing the proteins of interest from the flocculus.

* * * * *